(12) United States Patent
Groisman et al.

(10) Patent No.: US 8,372,358 B2
(45) Date of Patent: Feb. 12, 2013

(54) MICROFLUIDIC SYSTEM AND METHOD FOR USING SAME

(75) Inventors: Alexander Groisman, San Diego, CA (US); Edgar Gutierrez, San Diego, CA (US); Eugene Tkachenko, San Diego, CA (US); Mark H. Ginsberg, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 103 days.

(21) Appl. No.: 12/861,686

(22) Filed: Aug. 23, 2010

(65) Prior Publication Data

US 2011/0044865 A1 Feb. 24, 2011

Related U.S. Application Data

(60) Provisional application No. 61/236,017, filed on Aug. 21, 2009.

(51) Int. Cl.
*B01L 3/00* (2006.01)
*B01L 99/00* (2010.01)
(52) U.S. Cl. ....... 422/544; 422/502; 422/503; 422/68.1; 435/287.3
(58) Field of Classification Search .................... None
See application file for complete search history.

(56) References Cited

U.S. PATENT DOCUMENTS

| | | | |
|---|---|---|---|
| 6,554,991 B1* | 4/2003 | Goodman et al. | 204/613 |
| 8,202,719 B2* | 6/2012 | Meathrel et al. | 435/287.2 |
| 2004/0126279 A1* | 7/2004 | Renzi et al. | 422/100 |
| 2006/0101775 A1* | 5/2006 | Miyake et al. | 52/710 |
| 2010/0322826 A1* | 12/2010 | Locascio et al. | 422/103 |
| 2011/0117656 A1* | 5/2011 | Robole et al. | 436/43 |

* cited by examiner

*Primary Examiner* — In Suk Bullock
*Assistant Examiner* — Timothy G Kingan
(74) *Attorney, Agent, or Firm* — Eleanor M. Musick; Procopio, Cory, Hargreaves & Savitch LLP

(57) ABSTRACT

In a microfluidic system, a magnetic clamp for sealing a flexible microchannel chip includes a base formed from a magnetically-attractable material. The base supports a window for viewing the face of the microfluidic chip. A ring with magnets uniformly distributed around it is disposed over the base. A transparent disk attached to the top of the ring has an inlet and an outlet for introducing and removing a fluid medium into a cavity defined the disk, the window, the center opening of the ring and the base. An elastomer cushion is attached to the inner surface of the disk. The magnetic force between the base and the magnets on the ring compresses the cushion against the microfluidic chip so that the microchannels are sealed against the window with a uniform and reproducible pressure.

28 Claims, 16 Drawing Sheets

5 mm

MICROFLUIDIC SYSTEM AND METHOD FOR USING SAME

RELATED APPLICATIONS

This application claims the priority of U.S. Provisional Application No. 61/236,017, filed Aug. 21, 2009, which is incorporated herein by reference.

GOVERNMENT RIGHTS

This invention was made with government support under Grant No. NIRT 0608863 awarded by the National Science Foundation (NSF), and Grants No. HL078784 and No. AR27214 awarded by the National Institutes of Health (NIH). The government has certain rights in the invention.

FIELD OF THE INVENTION

The present invention relates to a device for reversibly sealing microfluidic chips against cover glasses and a method for using such a microfluidic system.

BACKGROUND OF THE INVENTION

Rolling and arrest of platelets on surfaces with various extracellular matrix (ECM) proteins under shear stress is central to hemostasis. Similarly, rolling and arrest of leukocytes (neutrophils and monocytes) on surfaces with various adhesion molecules plays an important role in inflammation and atherosclerosis. The two processes can be studied ex vivo by perfusion of blood over substrates with various coatings and monitoring the dynamics of rolling and arrest of platelets or leukocytes, as appropriate. An important component of both the dynamic platelet adhesion assay and the leukocyte rolling assays is the coating of the glass substrate, known as a flow chamber, with adhesion molecules: VWF, fibrinogen, and collagen for platelets, and selectins, chemokines, ICAM-1 and CAM-1 for leukocytes. Flow chambers have been in use since the early twentieth century for various tissue-culture applications, and were first used to study rolling and arrest in the 1980's.

Another application of flow chambers is the study of shear stress responses of endothelial cells. Endothelial cells form a monolayer on the interior surface of blood vessels and sense shear stress generated by blood flow. Endothelial cells respond to shear stress with rearrangements, vascular remodeling, and alterations of vascular tone and vascular permeability. Shear stress can modulate many functions of endothelial cells including gene expression, cell adhesion, proliferation, differentiation, migration, and cytoskeletal alignment relative to the direction of flow.

Perfusion chambers for experiments with live cells are among the most straightforward and versatile microfluidic devices. In addition to substantial reduction of the amounts of media and cells required for an experiment as compared to traditional flow chambers, microfluidic perfusion chambers offer numerous new capabilities. Those include the variation of composition of the perfusion medium across the microfluidic chip and in time, the capture of flowing cells using microfabricated weirs or posts, and generation of substrate coatings with customized micro-patterns. Microfluidic perfusion devices that are made of a cast PDMS (polydimethylsiloxane) chip sealed with a microscope cover glass also offer the advantages of compatibility with the standard high-resolution microscope objective lenses as well as low cost and disposability. Microfabrication makes it easy to produce tapered perfusion chambers, which generate varying shear stresses at the substrate.

A significant drawback, however, is that the loading of cells into such microfluidic devices can be a delicate task. If the cell stock is small, cells can be sensitive to hydrodynamic stresses, or a particular cell density on the substrate may need to be reached. The pre-assembled microfluidic devices that are commonly used for rolling and arrest studies are coated by perfusing the microchannels with solutions of the adhesion molecules and incubating the solutions in the microchannels. This coating procedure can make it difficult to measure and control the site density of the adhesion molecules. One solution to address this problem is to use excessive concentrations of adhesion molecules in an attempt to achieve some unknown saturated site density. The problem with this method is that, along with the flow shear stress, the site density is an essential experimental parameter. This approach also requires substantially more reagents and does not allow creation of substrate regions with different coatings on them. The ability to control the site density of the adhesion molecules should make it easier to emulate in vivo conditions, and potentially more importantly, to improve the repeatability of the assays and to provide new opportunities for detection of adhesion (and rolling) phenotypes of certain mutations and modifications of integrins and related molecules.

A different approach to address the site density problem is to incubate the glass substrate under a layer of solution with a known concentration of adhesion molecules. While this would be expected to improve control and reproducibility of the site density, a major obstacle is that microfluidic chips made of PDMS are normally sealed against dry cover glasses using either oxygen plasma or relatively high temperatures, both of which destroy biomolecular coating on the glass surface. Thus, the use of cover glasses with pre-coated surfaces requires finding a way to seal PDMS chips against wet cover glasses.

Two main techniques have been proposed to seal PDMS microchannel chips against wet substrates with cell cultures: mechanical clamping and vacuum suction, both of which introduce their own problems. The application of mechanical clamps usually involves poorly characterized and not completely reproducible mechanical stresses that may cause substantial deformations of microchannels, which may vary across the device. Sealing by vacuum suction is achieved by surrounding the "wet" microchannel array, containing media and cells, with a secondary network of "dry" microchannels connected to a source of vacuum. This technique has been used for short term experiments with endothelial cells and for long-term stem cell cultures. However, the application of vacuum could produce slow changes in the gas content of the wet channel medium that may be difficult to detect and quantify. Thus, both mechanical clamping and vacuum suction introduce variables into the experiment or assay that negatively impact accuracy and reproducibility.

Accordingly, the need remains for a device and method for sealing microchannel chips against wet substrates without damaging the cells or introducing conditions that can affect accuracy and reproducibility of the experiments. Further, a need remains for a method for perfusing microfluidic chips that provides control of site density for improved repeatability and expanded experimental applications.

SUMMARY OF THE INVENTION

In an exemplary embodiment, the inventive device has two basic components: a magnetic clamp and a specially-designed microfluidic chip. The magnetic clamp exerts a reproducible and uniform pressure on the microfluidic chip, achieving fast and reliable sealing with minimal mechanical perturbation to cells on the substrate. The chips are made of a relatively thin layer of a hard, flexible material to increase their flexibility so they conform to the substrate in spite of their relatively high hardness. The chips are used in combination with relatively thick and soft cushions.

The inventive combination can be used with a variety of microfluidic chips with adherent or non-adherent cells on the substrates to provide an advanced and versatile "lab on a chip" platform for research and clinical experiments, including shear stress response, chemotaxis, motility, and real-time microscopy.

In one aspect of the invention, the magnetic clamp includes a base with an open center, the base comprising a magnetically-attractable material. A window adapted for viewing the face of the microfluidic chip is supported within the open center. A ring disposed over the base has a center opening corresponding to the open center of the base. Magnets are distributed around the ring for generating a magnetic force drawing the ring toward the base. A transparent disk is disposed on top of the ring, the disk having an inlet and an outlet adapted for connection to a fluid medium reservoir for introducing and removing a fluid medium, wherein the disk, the window, the center opening of the ring and the open center of the base define a cavity for enclosing a microfluidic chip with the face of the microfluidic chip with at least one test region abutting the window. An elastomer cushion is disposed within the cavity between the disk and a backside of the microfluidic chip so that the magnetic force compresses the elastomer cushion against the microfluidic chip so that the at least one test region is sealed against the window.

Adjustable spacers are provided for creating a gap between the base and the ring to adjust compression of the elastomer cushion to control the pressure applied against the microfluidic chip. A channel having a first end and a second end extends through the cavity in fluid communication with each of the inlet and the outlet, with the second end terminating near an inner surface of the window so that the fluid medium is communicated to the microfluidic chip.

In one embodiment, the inventive combination comprises a steel base that holds the cover glass and a cover that houses a set of magnets and holds the chip. The magnetic clamp produces small deformations of the microchannels of the chip resulting in minimal variations of substrate shear stress, while providing reliable sealing up to pressures of 40 kPa inside the microfluidic device. The clamp/chip combination can be used with any type of microfluidic network of an appropriate size, as long as inlet and outlet ports of the network match those in the cover. Application of controlled differential pressures between the inlet and outlet makes it possible to generate flows with a broad range of speeds and substrate shear stresses, as well as pulsatile flows with well-defined characteristics. The sealing of the microfluidic devices with the magnetic clamp is simple and fast. The clamp can also be closed slowly by using a set of thumb screws in the cover, thus minimizing the flow and hydrodynamic stresses generated during the sealing process.

In another aspect, the invention makes it possible to produce molecular coatings with well defined boundaries on substrates with controlled site densities of the molecules. The coatings are produced using removable stencils or masks, which are <1 mm thick sheets of silicone elastomer in which windows have been formed. Using the stencils, minimal amounts of solutions of the molecules are required. In addition, a single substrate, such as a cover glass, can be divided into a number of distinct regions of precisely defined dimensions with sharp boundaries. The distinct regions, each effectively a "micro-cuvette", can be created using small volumes (~10 μL) of different solutions or molecules applied with a micropipette or microsyringe. After a period of incubation, the cover is removed, the micro-cuvettes are purged and rinsed, and the stencil is separated from the substrate, distinct regions with uniform surface densities of the deposited molecules. The final density of the molecules deposited on the substrate is highly reproducible and is controlled by their concentration in the solution and by the time of incubation.

The coated substrates can then be used with microfluidic devices that are sealed against the wet coated substrates with the aid of the inventive magnetic clamp.

Applications of the microfluidic chips and coating stencils according to the present invention include study of the rolling and arrest of leukocytes on substrates with various coatings under shear flow. A single device can have test chambers (microchannels) with different values of shear stress covering a representative physiological range. The rolling and arrest assays can be performed with whole mammalian blood, including blood coming directly from an anesthetized laboratory animal. A single device can be used to simultaneously test two blood samples, and a single blood sample can be perfused over regions with different coatings. The molecules deposited on the substrate can be selectins, chemokines, and cell adhesion molecules (ICAM and VCAM). Sharp boundaries between differently coated regions can help follow the dynamics of changes in rolling and arrest of cells upon their exposure to a new type of molecules on the substrate. Another application is the rolling and arrest of platelets on substrates with various molecular coatings in shear flow. The molecules that can be coated on the substrate include collagen, fibrinogen, and van Willebrand factor (vWF). A single device can have channels with a broad range of shear stresses and a single device can be used to simultaneously test the rolling and adhesion of platelets from two separate blood samples, and/or platelets to differently coated substrates.

BRIEF DESCRIPTION OF THE DRAWINGS

In FIG. 4a, magnetic force (in Kg) is plotted as a function of the distance between the cover and the base for different numbers of magnets. FIG. 4b is a plot of the pressure inside the microfluidic device at which it starts leaking (burst pressure) as a function of the number of magnets per well. FIG. 4c is a plot of height of resistance channels and test regions as a function of the number of magnets per well. FIG. 4d shows substrate shear stress, τ, in a test region for different numbers of magnets per well.

DETAILED DESCRIPTION OF THE INVENTION

Figure 1:
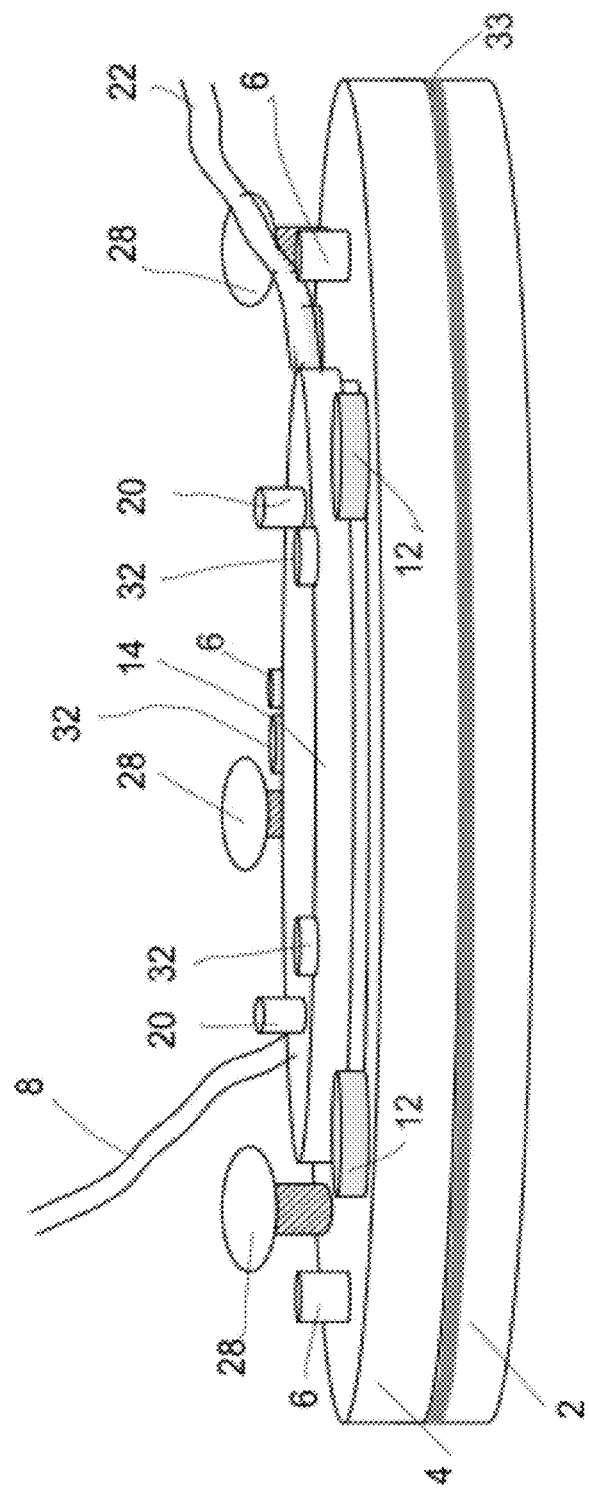
FIG. 1 is a perspective view of the magnetic clamp assembly according to the present invention.
Figure 2:
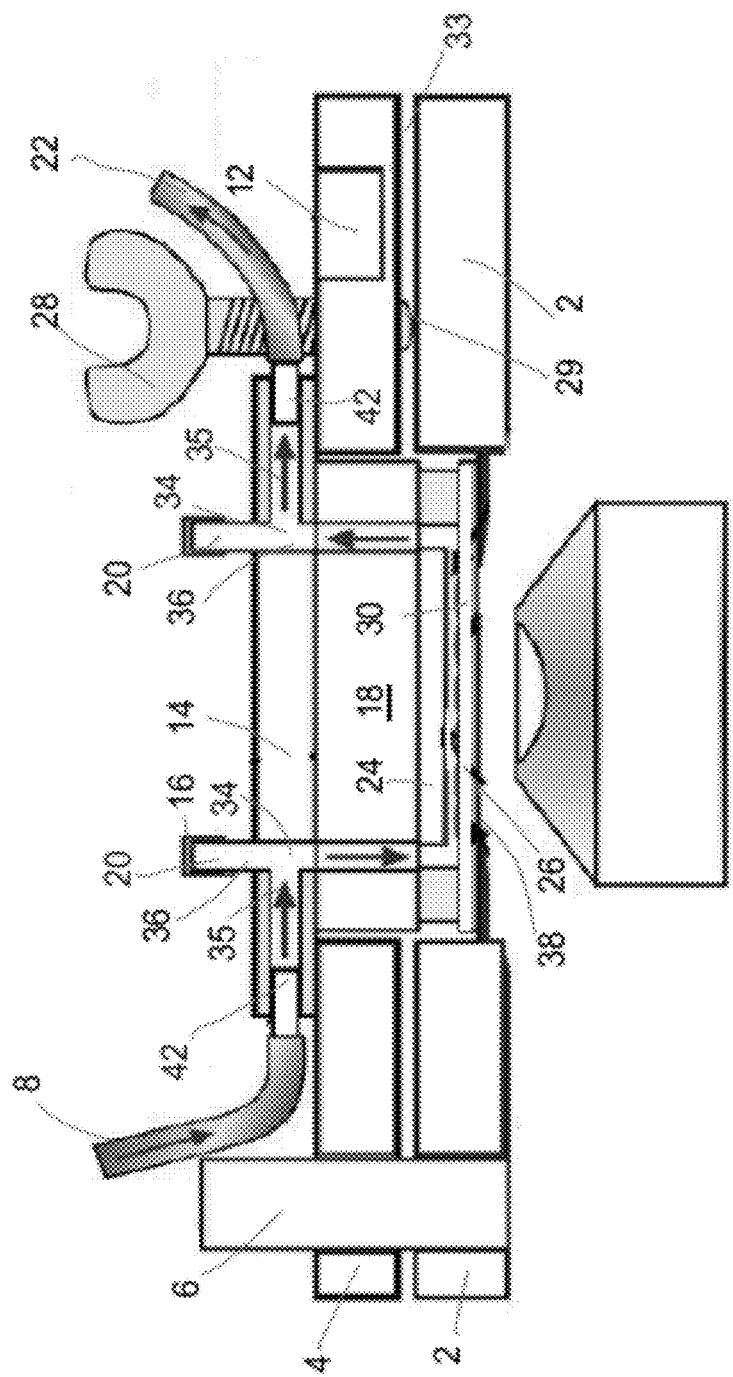
FIG. 2 is a schematic drawing of cross-section of assembled clamp.

As illustrated in FIGS. 1 and 2, the inventive magnetic clamp 10 has two primary components: the base 2 and the cover. The base 2 is a ring formed from a magnetically-attractable metal. The cover is an assembly of a ring 4 and a plastic, e.g., acrylic, disk 14 which sits over the center of the ring to define a cavity. An elastomer cushion 18 fits within the cavity defined by the interior of ring 4 and disk 14 so that the chip 24 with cells 30 is sandwiched between the cushion and an optically transparent window 26, e.g., a cover glass, which is supported in the bottom of the base 2. Alignment features, in this case, pins 6 and corresponding bores or recesses, are provided in one or both of the base and ring to align the two pieces. Magnets 12 that are sufficiently strong to attract the base material are attached to ring 4. As illustrated, magnets 12 are inserted into recesses that are uniformly spaced around the top of ring 4, however, other attachment methods may be used. Threaded bores formed in ring 4 receive thumb screws 28 inserted through the threaded bores to allow adjustment of the gap between the ring and the base to counter the magnetic force between the cover and the base. A plastic or polymer disk 14, preferably transparent, is attached to the top of ring 4 by way of fasteners. As illustrated, screws 32 extend through bores in disk 14 to screw into threaded recesses in the top of ring 4 to releasably attach the disk to the ring. Two channels 36 extend vertically through the full thickness of disk 14 to the space between the chip 24 and the cover glass 24 to provide fluid inlet and outlet access to the cells 30. Inlet tubing 8 and outlet tubing 22 are connected to the channels 36 via T-connectors 34 which are formed by creating bores 35 through the sides of the disk to intersect channels 36. The upper ends of the channels 36 have small, tubular inserts, which extend above the upper surface of disk 14 to serve as bubble traps 20. The bubble traps may be releasably sealed at their upper ends by plugs 16.

In a test set-up, the dimensions of the device are selected to be similar to those of a commercially-available perfusion device with a magnetic clamp, Chamlide™ (by LCI Corp., Seoul, Korea). The base 2 is a 64 mm diameter, 3 mm thick disk made of grade 410 magnetic stainless steel. The base 2 has a 29 mm diameter, 1 mm deep groove on its top side, a 15 mm diameter opening 38 in the center, and a 0.15 mm deep step around the opening to hold a circular 25 mm microscope cover glass. The opening 38 is shallowly tapered toward the bottom of the base to allow good access of microscope objective lenses to the cover glass. The base 2 has three ground steel pins 6, each ³⁄₁₆" diameter, pressure-inserted into openings formed at uniform spacings. The cover assembly includes a 64 mm diameter, 4.5 mm thick brass ring and a 38 mm diameter, 6 mm thick Plexiglas® (acrylic) disk, which may be fastened to the ring 4 with four screws 32. The brass ring 4 has 6 wells to house 6.35 mm (¼") diameter, 3.2 mm (⅛") thick neodymium magnets 12 (Magcraft®, commercially available from National Imports LLC, Vienna, Va.) Each well has one magnet 12 permanently glued into it. Extra magnets can be added or removed to vary the magnetic force between the cover and the base. The ring 4 has three holes matching the pins 6 in the base to ensure concentric assembly of the setup and smooth sliding of the cover toward the base. The ring 4 also has three threaded bores for receiving M3-0.5 thumb screws 28. The screws 28, which have rounded tips 29 to butt against the upper surface of base 2, support the cover 4 to counter the magnetic force, providing means for controlling the spacing 33 between the cover and the base, allowing adjustment of the spacing by small increments.

The Plexiglas® disk 14 has two bores 35 formed through its sides, perpendicular to the plane of the disk, with short segments 42 of steel hypodermic tubing inserted into the bores. The steel tubing inserts 42 connect through lines of PVC tubing to reservoirs (not shown) with the medium fed in through inlet tubing 8 to the micro fluidic device 24 and drawn off from the device via outlet tubing 22. The side bores are connected to 1.5 mm diameter vertical holes 36 drilled 8.5 mm from the center that opened at the top of the disk to bubble traps 20, which were closed by plugs 16. At the bottom of the disk 14, the vertical holes 36 are connected to through-holes in an ~27 mm, 5 mm thick flat-parallel slab of a transparent soft silicone rubber 18 that was bonded to the disk 14 to act as a cushion between the disk and the PDMS microchannel chip 24. The soft cushion 18 (Shore A durometer 20 vs. 50 for the microchannel chip) converts the magnetic force pulling the cover toward the base into a uniform pressure applied to the top of the chip. The chips 24 used with the clamp had microchannels engraved on their bottom side facing the cover glass 26. The chips have a diameter of ~24.5 mm, matching standard 25 mm microscope cover glasses, and the inlet and outlet through-holes in the chips (8.5 mm from the center) are aligned with those in the cushion. The PDMS chips has a relatively small thickness of ~1.2 mm to achieve a low bending modulus for uniform distribution of the pressure from the cushion over the chip surface and for good contact between the chip 24 and the cover glass 26.

To fabricate the cushion 18, four 1.5 mm diameter, 4.8 mm tall stainless steel posts were glued to the surface of a silicon wafer at distances of 8.5 mm from a common center. The wafer was placed onto a leveled horizontal surface and a silicone pre-polymer (10:1 mixture of base and activator of XP-565 rubber by Silicones Inc., High Point, N.C.) was slowly poured onto the wafer, until the posts were completely submerged and the surface of the pre-polymer on top of them was flat. The silicone was slowly cured on a leveled substrate in a 50° C. oven and subsequently separated from the wafer. The vertical holes produced by the pins were opened at the top, and the silicon cast was punched by a sharpened steel tube, ~27 mm diameter, that was centered with respect to the holes. A completed cushion 18 had flat upper and lower surfaces, and its thickness was uniform to within ~0.1 mm. To bond the cushion to the acrylic disk 14, a droplet of PDMS pre-polymer (Sylgard 184 by Dow Corning) was dispensed onto the center of the disk 14, the cushion 18 was placed on top of the droplet and pressed against the disk, and the assembly was baked for 90 min in a 80° C. oven to cure the PDMS. (The disk and the cushion had 4 matching holes each, but only two juxtaposed holes were connected to the PDMS chips used in the test set-up.) The disk 14, cushion 18, and PDMS chip 24 were all optically clear and had flat-parallel surfaces, making the setup compatible with brightfield and phase-contrast microscopy.

Figure 3:
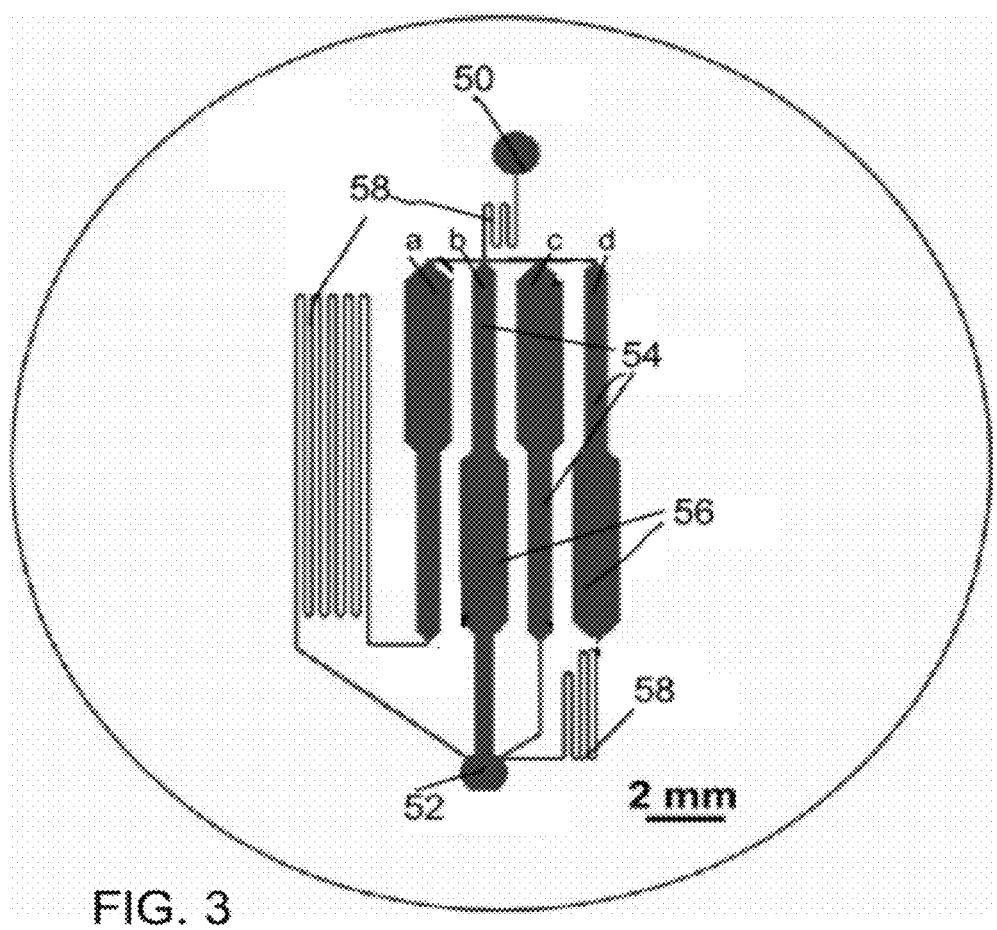
FIG. 3 is a diagrammatic view of the layout of microchannels in the microfluidic device.

The use of microfabricated PDMS chips instead of gaskets makes it possible to adjust the flow resistance between the inlet and outlet, enabling parallel channel lines with different substrate shear stresses in channels with identical cross-sections. FIG. 3 provides one possible layout for a microfluidic chip for use with the inventive magnetic clamp. An exemplary chip has a network of 75 μm deep microchannels, which were cast of PDMS (Sylgard 184 by Dow Corning) using a photo-lithographically fabricated master mold. To produce the mold, a 127 mm (5") silicon wafer was spin-coated with a 75 μm thick layer of a UV-curable epoxy (SU8-2050 by Microchem), exposed to UV-light through a specially designed photomask (photo-plotted at a resolution of 20,000 dpi), and developed. PDMS pre-polymer (15 g) was poured onto the mold, and the mold was placed onto a level horizontal surface in a 65° C. oven for 30 min to allow the pre-polymer to reflow, spread in an even layer, and slowly cure. To complete the curing, the mold was placed into an 80° C. oven for 1 hr. The cured PDMS cast was separated from the mold, individual chips were punched from the cast with a ~24.5 mm diameter sharpened steel tube (the cast had 24.5 mm rings engraved in it for concentric punching), and the inlet 50 and outlet 52 holes were punched in the chips with a gauge 14 luer stub. To increase the hardness and Young's modulus of the chips, they were baked for 30 min in a 150° C. oven. Completed chips had a thickness of ~1.2 mm, which was typically uniform to better than 0.05 mm.

Referring still to FIG. 3, the microchannel network of chip 24 had four separate lines of channel connecting the inlet and the outlet, indicated as channels a, b, c and d. Each channel line had a 0.6 mm wide test region 54 and a 1.2 mm wide test region 56, for studying shear stress responses of endothelial cells. The mean flow velocity and substrate shear stress, $\tau$, in two test regions of each channel line differed by a factor of two because of the 2-fold difference in the test region widths. The device also had 100 μm wide resistance channels 58 that were designed to provide a 4-fold difference in the total hydrodynamic resistance between different channel lines and 4-fold variation of the volumetric flow rate through them. Altogether, the device was designed to have 2-fold variation of $\tau$ between test regions with consecutive numbers, and a total 128-fold range in $\tau$. Numerical modeling with FemLab® software (from COMSOL AB) indicated that for a fully developed laminar flow in a 75 μm deep channel line, the ratio of $\tau$ in internal regions (away from the side walls) of the 0.6 mm and 1.2 mm wide rectilinear channels is 2.06 (slightly greater than 2 due to side wall effects). The modeling also showed that the substrate shear stress in both channels is reduced near the side walls. Nevertheless, $\tau$ is within 5% of its maximal value (attained in the middle) in a 0.47 mm wide internal area of the 0.6 mm wide channel and in a 1.06 mm wide internal area of the 1.2 mm wide channel. Therefore, cells on the substrate in each of the two internal areas are expected to experience a nearly uniform mechanical stimulus.

The following examples demonstrate the utility of the inventive magnetic clamp assembly.

EXAMPLE 1

Migration and Alignment of Cells

The microfluidic device used in this test had a microchannel network with 8 separate rectilinear test regions and with surface shear stress varying by a factor of ~2 between each region, thus covering a 128-fold range in the shear stress, from low venous to arterial.

Human Umbilical Vein Endothelial Cells (HUVECs) (Cambrex) were grown in endothelial basal medium (EBM-2) containing endothelial growth factor supplements (EGM-2 bullet kit, Cambrex). Circular 25 mm, #2 cover glasses were rinsed in methanol, spin-dried, treated for 5 seconds with air plasma using a laboratory corona treater (BD-20AC, by Electro-Technic Products, Inc., IL), and coated with fibronectin by placing a droplet of a 5 μg/ml fibronectin solution onto a cover glass and incubating it for 1 hr. The cover glass surface was subsequently blocked by 30 min incubation under a 1% solution of heat-denatured BSA. An estimated $0.5 \times 10^6$ HUVEC cells were plated on the fibronectin-coated cover glass and incubated for 48-72 hours to form monolayer.

The medium fed to the inlet and drawn off from the outlet was kept in identical plastic syringes (10 or 60 cc for tests of flow in the device and 140 cc for extended perfusions with endothelial monolayers), which were held upright with the luer connectors at the bottom. The syringes were connected to the device inlet and outlet through blunt hypodermic needles and ~1 m long segments of PVC tubing with the inner diameter of 1 mm. The syringe connected to the outlet was held at a height of ~10 cm above the level of the device to ensure positive pressure everywhere inside the device and prevent formation of air bubbles. The syringe connected to the inlet was attached to a stage sliding along a vertical rail. The flow in the microfluidic device was driven by a differential hydrostatic pressure between the inlet and outlet, $\Delta P = \rho g \Delta h$ (where $\rho = 1$ g/cm$^3$ is the density of the medium), which was set by adjusting the difference between the levels of the media in the two syringes, $\Delta h$, and was controlled within 5 Pa (0.5 mm in $\Delta h$). The syringes were covered at the top to reduce evaporation but were normally vented to the atmosphere (not sealed).

Measurements of flow velocity and channel deformation in the device were performed on a Nikon Diaphot inverted fluorescence microscope equipped with a 100 W mercury light source. A Sony XCD-X900 IEEE 1394 camera (1280×960 pixel CCD array, 7.5 frames/s) or a Marlin-F033b IEEE 1394 camera (640×480 pixel CCD array, 60 frames/s) were used for video microscopy. Flow velocities in the microfluidic device were measured with aqueous suspensions of 2 μm green fluorescent tracer particles. The microscope was focused at the mid-plane of microchannels, and the maximal flow velocities, $v_{max}$, were evaluated by measuring the lengths of longest streaklines produced by the beads. The fluorescence light source in the channel deformation tests was a high power blue LED (Royal Blue Luxeon V by Lumileds; central wavelength 455 nm) inserted into a modified Nikon lamp house. The LED was powered by a regulated DC supply and provided stable fluorescence illumination (<1% variation of intensity over several hours).

The experiments with endothelial cells were performed on a Nikon TE2000 inverted fluorescence microscope equipped with a cooled digital camera (CoolSnapHQ, by Roper Scientific) and an environmental enclosure. Time-lapse images of cells in various regions were acquired in parallel using a computer-controlled XYZ-motorized stage (LUDL 99S000). The stage was programmed to move in loops with stops at the positions of interest and was interfaced with the image acquisition using a routine in QEDinVivo (Media Cybernetics, Bethesda, Md.).

The environmental enclosure maintained the temperature at 37±0.5° C., which was appropriate for endothelial cells. The temperature stabilization also minimized the drift of focus in the microscope. In addition to the microscope enclosure, a stage enclosure was placed onto the motorized microscope stage on top of the magnetic clamp setup. Continuous flow of humidified air with 5% $CO_2$ through the stage enclosure created a stable and nearly optimal gas environment around the PDMS microfluidic chip that helped in maintaining cell viability. The syringes with perfusion media connected to the inlet and outlet were kept outside of the microscope enclosure. To prevent formation of gas bubbles in the device due to reduction of gas solubility caused by heating of the medium from room temperature to 37° C., the syringe connected to the inlet was warmed to ~37° C. by using a heat strip and a temperature controller. Before an experiment was started, air with 5% $CO_2$ was bubbled through the perfusion medium in the inlet syringe to set the gas content of the medium and to bring its pH to 7.4. To maintain both the pH and the gas content constant during prolonged perfusions, a slow stream of air with 5% $CO_2$ was continuously blown above the medium surface in the inlet syringe.

Before the magnetic clamp was assembled, the engraved surface of the PDMS chip was treated with air plasma (to make it more wettable) and the back side of the chip was attached to the cushion on the clamp cover. A syringe with ~60 mL of perfusion medium was connected to the inlet, and a syringe with a small amount of the medium was connected to the outlet through ~1 m long lines of PVC tubing. Once the flow of the medium reached the cover of the magnetic clamp, filled the bubble traps, and flooded the surface of the PDMS chip, the bubble traps were closed with plugs, and both tubing lines were clamped to stop the flow through them. The cover glass with endothelium monolayer and with a thin layer of the perfusion medium on top of it was placed onto the base of the clamp. The thumb screws in the cover of the clamp were completely retracted, the holes of the cover were aligned with the pins of the base, and the cover was allowed to slide down under the action of magnetic force and gravity. The setup closing was accompanied by flow of the medium squeezed from between the chip and the cover glass. To prevent damage to the endothelium due to hydrodynamic stresses generated by the flow, it was important to unclamp the inlet and outlet PVC tubing lines before closing of the setup, thus providing a relatively low-resistance escape route for the medium. To separate the cover from the base after completion of a perfusion assay, the thumb screws were turned clockwise in a cyclic order, thus lifting the cover and gradually reducing the magnetic force.

A major concern about clamping as a method for sealing a microfluidic device is that it might cause substantial deformations of microchannels that would be inconsistent between different tests and could significantly alter the pattern of flow in the device. In the proposed magnetic setup, the clamping force is reproducible and depends only on the number of magnets and on the distance d between the cover and the base of the clamp. To measure the magnetic force between the cover and the base, the clamp was firmly attached to the top of an electronic balance, and the cover was slowly pulled upwards by three soft springs until it detached from the base. The magnetic force was quantified as the difference in readings of the balances between the time before the pulling started and a time immediately before the cover detached from the base. The measurements, which are plotted in FIG. 4a, were done with different numbers of magnets in the wells of the cover (always the same number in each of the 6 wells) and at different d. The magnitude of d was set by placing spacers of known thickness (brass shim) between the cover and the base with no other contact between the two parts. A standard value of d=0.7 mm was used for the setup, with 1-5 magnets per well providing clamping forces of 0.27-0.95 Kg (FIG. 4a, inset) and pressures of 5.6-20 kPa on the 24.5 mm circular PDMS chips.

Figure 4A:
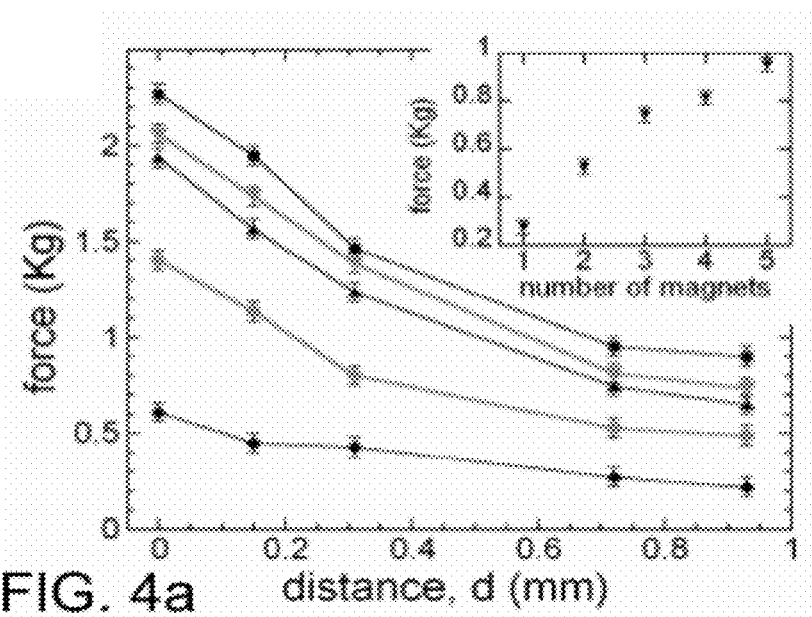
FIGS. 4a-4d are plots showing the results of mechanical tests of the clamp setup.
Figure 4B:
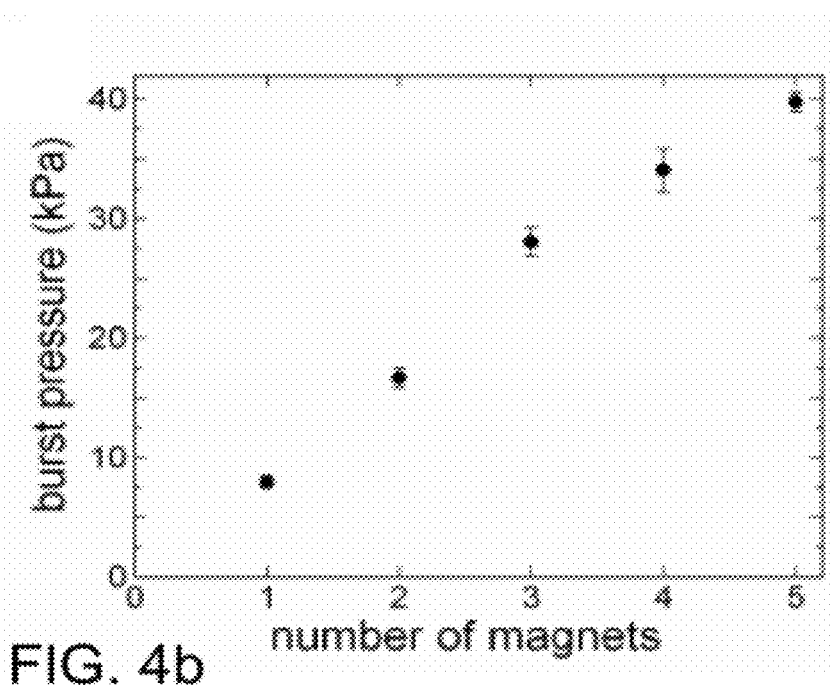

The quality of sealing produced by the clamp is measured by the maximal internal pressure a sealed device can withstand without leaking. To quantify this "burst" pressure, the PDMS chip of FIG. 3 was sealed against a plain #2 cover glass. The sealed device was filled with water and the inlet and the outlet were connected to the same regulated source of compressed air. The pressure was gradually increased until the microfluidic device leaked. As expected, the burst pressure increased with the number of magnets, as shown by FIG. 4b. The values of the burst pressure were systematically higher than the pressure exerted onto the PDMS chip by the clamp cover, e.g., 28 kPa vs. 15 kPa for 3 magnets and 40 kPa vs. 20 kPa for 5 magnets. The added resistance to the pressure might have originated from adhesive forces between the surfaces of the cover glass and PDMS chip.

To evaluate the deformation of microchannels caused by the pressure exerted onto the chip by the clamp, the device was filled with a solution of fluorescent dye (6 ppm by weight of fluorescein isothiocyanate, FITC, by Sigma, St. Louis, Mo.) in a pH7 phosphate buffer and the intensity of its fluorescence was measured. At a constant microchannel height of 75 μm, the fluorescence intensity of 0-8 ppm FITC solutions, which was measured with a 6.3×/0.2 objective, was a linear function of concentration. The fluorescence intensity of a 6 ppm solution of FITC measured in three microchannels with depths of 20, 100 and 200 μm was a linear function of the channel depth within ~3% measurement error. Therefore, fluorescence intensity of a 6 ppm FITC solution in the proposed device was expected to be a linear function of the local channel height, h. The measurements were done in four 1.2 mm wide channels (56 in FIG. 3), four 0.6 mm wide channels (54 in FIG. 3), and four 100 μm wide channels (58 in FIG. 3). To have a reference point for the original channel height of 75 μm (no channel deformation), the PDMS chip was first bonded to a dry cover glass, then filled with the FITC solution. Fluorescence was measured in the channels without the cover applied. The test was subsequently repeated with the clamp and 1-5 magnets in each well of the cover. The results are plotted in FIG. 4c. The sagging of the channel roofs was minimal near the channel walls and maximal in the middle of the channels. The sagging increased with both the number of magnets and channel width. Nevertheless, even for the 1.2 mm wide channels, the roof sagging in the middle of the channels was only ~5% of the channel height with 2 magnets (burst pressure of 16.5 kPa) and remained limited to ~9% with 5 magnets (burst pressure of 40 kPa). The height reduction was about half as large for the 100 μm wide resistance channels. Further reduction of the channel deformation without reduction of the device burst pressure might be achieved by using thinner chips made of a harder formulation of PDMS. Therefore, the proposed magnetic clamp can potentially be used for PDMS chips with microchannel heights substantially less than 75 μm, making it suitable for a broad range of micro fluidic applications.

Figure 4C:
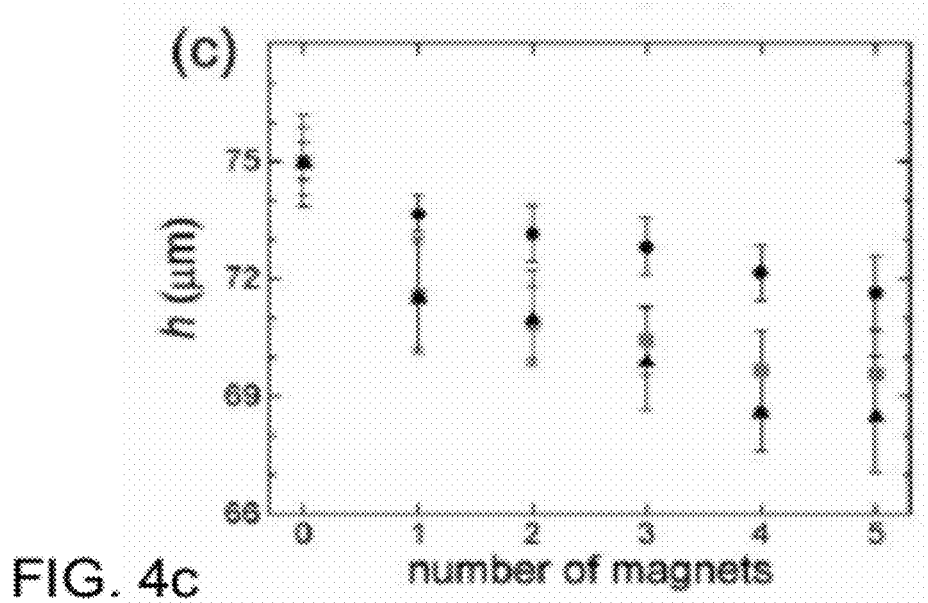
Figure 4D:
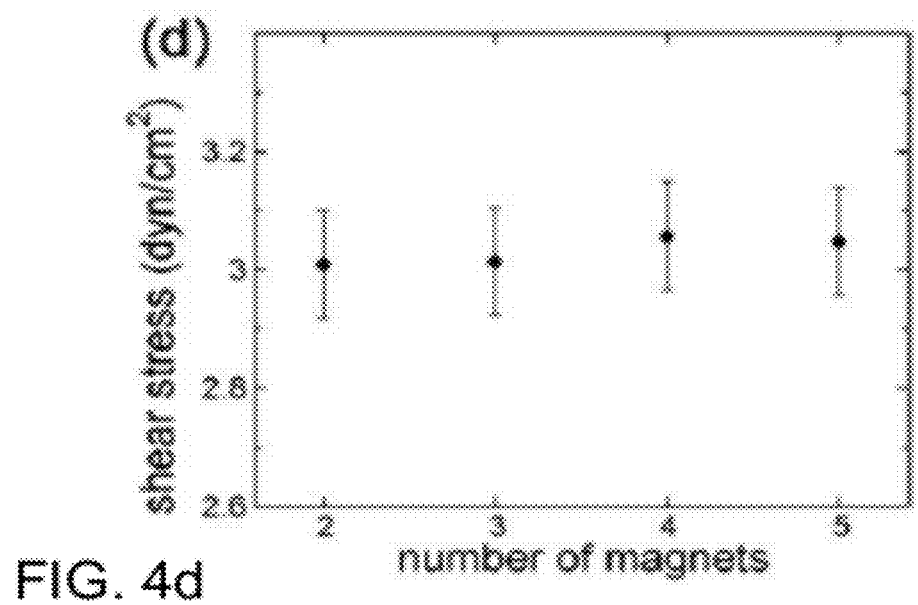

To evaluate the influence of the channel deformation upon substrate shear stress, τ, during perfusion, the maximal velocity of flow, $v_{max}$, was measured in one of the test regions 54 (nearest outlet 52) at a differential pressure $\Delta P=2$ kPa between the inlet 50 and outlet 52. The measurements were performed with 2-5 magnets and the obtained values of $v_{max}$ were used to calculate the surface shear stress as $\tau=4\eta v_{max}/h$, where $\eta=0.01$ Ps was the viscosity of water at room temperature (20° C.) and h was the channel height measured in the previous test (FIG. 4d). The augmentation of the magnetic force from 0.52 to 0.95 Kg (cf. FIG. 4a inset) and the resulting reduction of the channel height by ~4% (cf. FIG. 4b) had little effect on $\tau$ (~1% variation). The change in $\tau$ was so small most likely because the rate of flow through the test regions primarily depended on the flow resistance of 100 μm wide channels, which suffered about half as much roof sagging as the test regions themselves (FIG. 4c).

Based on the results of the above tests, 3 magnets per well were chosen. With a given number of magnets, the clamping force can only vary as a result of changes in the thickness of the PDMS chips used with the setup, which cause variations in d. The chip thickness variations are easy to limit to <0.2 mm, resulting in d within 0.5-0.9 mm and the clamping force in a range of 0.66-0.98 Kg (pressure 14-20 kPa; FIG. 4a). From the data shown in FIGS. 4c and 4d, the mean sagging of the microchannel roofs in this range of clamping force is expected to be <7 μm and <6 μm for 1.2 mm and 0.6 wide test regions, respectively, and is expected to lead to a minimal variation in $\tau$ in the test regions. The lowest value of the clamping force, 0.66 Kg, corresponds to a burst pressure of ~24 kPa, which is almost an order of magnitude higher than the pressure $\Delta P=2.75$ kPa required to generate a substrate shear stress of 9 dyn/cm$^2$ (see below), a value characteristic for arterial blood flow. Therefore, the magnetic clamp achieves reliable sealing and makes it possible to perform consistent perfusion experiments with sufficiently high levels of surface shear stress.

Maximal flow velocities, $v_{max}$, were measured in the test regions of the device at a differential pressure $\Delta P=2.75$ kPa at the room temperature by feeding to the inlet water seeded with tracer particles (2 μm fluorescent polystyrene beads). Streaklines produced by the particles were photographed under fluorescence illumination, and the value of $v_{max}$ was obtained by dividing the maximal length of the streaklines (measured at the central axis of the channel) by the exposure time. The substrate shear stress in internal areas of the test regions was then calculated as $\tau=4\eta v_{max}/h$. The value of $v_{max}$ was highest in test region 8, where it was 19 mm/s, corresponding to a Reynolds number $Re=v_{max}\rho h/\eta=0.14$, where $\rho=1$ g/cm$^3$ is the density of water. This relatively low value of Re indicated a stable laminar flow with a linear dependence of $\tau$ on $\Delta P$. The uncertainty of $\tau$ was estimated as ~4% and was due to uncertainties in measurements of the streakline lengths and of the microchannel heights. The values of $\tau$ measured in consecutive test regions of the device closely followed a geometric progression with the common ratio of 2, deviating from the progression by <13% and spanning a total range of 127 (Table 1), essentially the same as the design target value of 128. The shear stresses in the test regions, 0.07-9 dyn/cm$^2$, were chosen to cover a range from low venous to arterial shear stresses in human circulation. It should be noted that for a laminar flow driven by a given differential pressure, $\Delta P$, the substrate shear stress, $\tau$, is independent of the viscosity of the fluid. For example, for a flow in wide and shallow rectilinear channel of length L, it is $\tau=\Delta Ph/(2L)$. Therefore, the results on $\tau$ obtained at the room temperature, listed in Table 1 below, were directly applicable to experiments with endothelial cells at 37° C., when the fluid viscosity was ~30% lower.

Because endothelial cells had strong adhesion to the substrate, no special care was required when sealing the device, other than opening the connections of the microfluidic chip to the inlet and outlet medium reservoirs. Nevertheless, to avoid unwanted exposure of cells to high shear stresses during the device sealing and for potential perfusion assays with weakly adherent cells, it is desirable to have a means to minimize hydrodynamic stresses during sealing of the device. To reduce stresses during the sealing, the three thumb screws in the cover were set to an initial distance of d=2 mm between the chip and cover glass. After the clamp cover was placed in its initial position, the thumb screws were turned counter-clockwise by equal angles in a cyclic order, leading to a gradual approach of the chip to the cover glass. For two parallel disks (the chip and cover glass) approaching each other at a constant speed, $v_z$, the flow of the liquid squeezed out from the space between the disks produces substrate shear stress, $\tau=3\eta v_z r/z^2$, that is proportional to the radial coordinate, r, and inversely proportional to the square of the distance between the disks, z. (For the microfluidic device, this dependence is expected to be modified starting from distances on the order of the microchannel height, h=75 μm). Therefore, the speed of approach was reduced as the distance, z, became smaller. Steps in z as small as 10 μm were made by turning a single screw (0.5 mm pitch) by ~20°.

Figure 5:
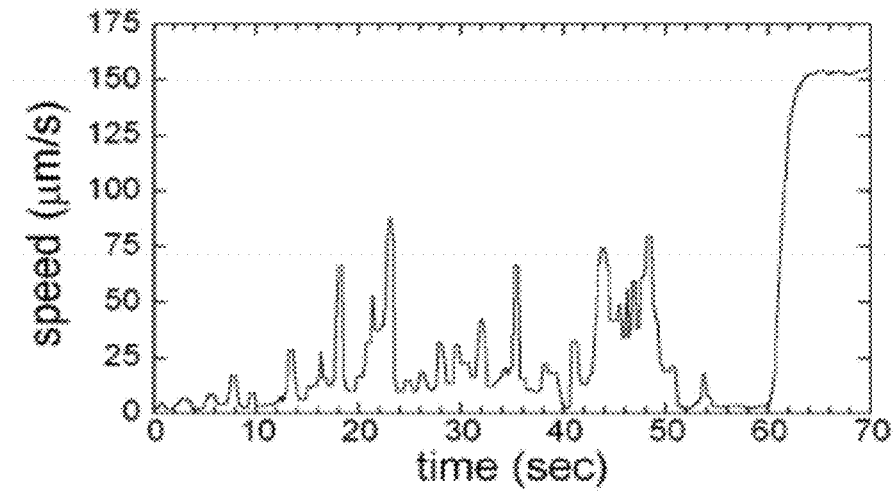
FIG. 5 is a plot of the mean speeds of polystyrene beads at the substrate in a test region during a final stage of closing of the magnetic clamp (time=0-56 sec) and after the setup is closed.

To evaluate $\tau$, an aqueous suspension of 10 μm red fluorescent polystyrene beads (with a density of 1.05 g/cm$^3$ and fast sedimentation) was deposited onto the cover glass and their motion tracked under a microscope. The beads stayed at the substrate, but did not adhere to it. Therefore, their speed was expected to be proportional to $\tau$. As shown in FIG. 5, the tracking of beads in the downstream part of test region 3 with r≈5 mm (the highest value for the entire area of test regions) indicated that their speed never exceeded 100 μm/s, as the microfluidic chip approached the cover glass. A subsequently started flow (time>60 sec in FIG. 5), which was driven by a differential pressure $\Delta P=2.75$ kPa and produced a substrate shear stress $\tau=0.25$ dyn/cm$^2$ (cf. Table 1), resulted in a collective motion of the beads at ~150 μm/s. Therefore, during the sealing of the device, the substrate shear stress was limited by ~0.17 dyn/cm$^2$. This level of shear stress is expected to be sufficiently low, even for weakly adherent cells such as human embryonic kidney cells and HL-60 cells. When applied for a short interval, the shear stress should cause minimal perturbation to neuronal growth cones. After the device was sealed, the number of beads in the field of view was reduced by less than a third compared with the initial number of beads. Therefore, for some experiments, it may be practical to close the clamp immediately after cells from the deposited suspension sediment onto the cover glass, without letting the cells spread and attach to the substrate. In addition, the magnetic clamp setup may be suitable for experiments with non-adherent cells that would be confined by weirs or traps after the device is sealed.

Blood flow in the vasculature and the shear stress at the endothelium are inherently pulsatile. The ratio between the pulsing and constant parts of the shear stress varies over the vasculature, being generally higher in arteries than in veins, and the pulsing frequency varies in time as the heartbeat period changes. Pulses in the shear stress are believed to be an important part of the mechanical stimulus experienced by endothelium in-vivo. Therefore, a close emulation of in-vivo flow conditions may require generation of shear stress pulses of controllable duration and amplitude. To generate a pulsatile flow in the microfluidic device, a rubber plug with a segment of PVC tubing was inserted into the syringe feeding the inlet, and the other end of the tubing was connected to the outlet of a solenoid valve with a low flow resistance and 7 ms switching time (P251SS-012-D by Ingersoll-Rand). One inlet of the valve was connected to a regulated source of compressed air set at a pressure $P_1$=1.4 kPa; the other inlet was vented to the atmosphere. The valve was periodically switched on and off using a home-made driver and a square wave signal from a function generator. In addition, the inlet syringe was set at a level 28 cm above the outlet syringe, generating a constant differential pressure $\Delta P_0$=2.8 kPa between the inlet and outlet. The resulting differential pressure was $\Delta P_0+\Delta P(t)$, where $\Delta P(t)$ was equal to $P_1$, when the valve was on (connecting the syringe to the pressurized air), and to zero, when the valve was off (venting the syringe to the atmosphere). Importantly, the period of pulsing and the ratio between the pulsatile and static parts, $P_1/\Delta P_0$, could be independently varied and controlled. The characteristic time of establishment of a laminar flow profile, estimated as the viscous diffusion time $t_{vd}=h^2\rho/\eta$, was 0.006 sec. Therefore, for physiologically relevant pulsing frequencies (0.5-3 Hz), variations of the substrate shear stress, $\tau$, were expected to follow the variations of the driving pressure with a minimal delay. Hence, $\tau$ in a given test region was expected to be proportional to $\Delta P_0+\Delta P(t)$ with the same coefficient of proportionality as between the values of $\tau$ and $\Delta P$ in Table 1, and the flow in the microchannels was expected to have a developed laminar profile (with $\tau=4\eta v_{max}/h$) at practically all times.

Figure 6:
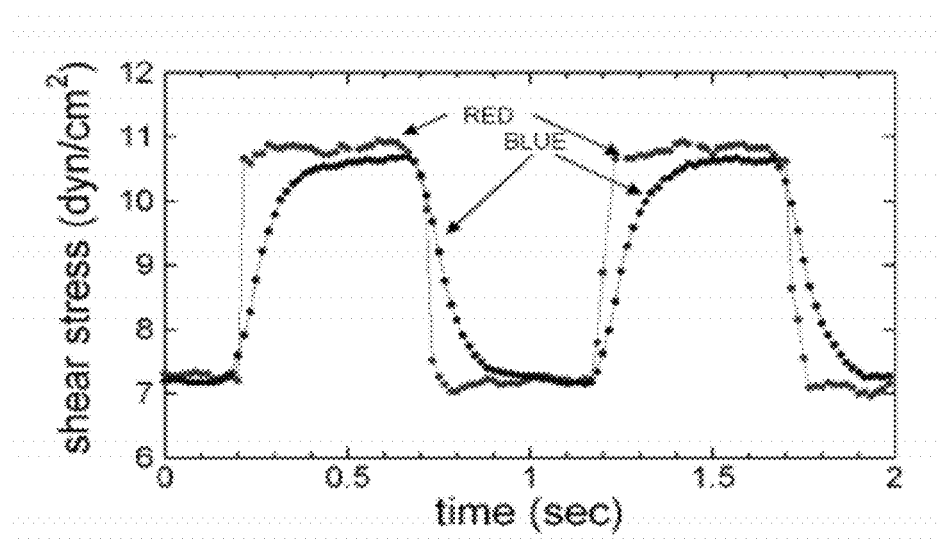
FIG. 6 is a plot of substrate shear stress, τ, in a test region as a function of time, where lower and upper curves represent the pressure switching with and without a pneumatic delay RC-circuit, respectively.

A pulsing period of ~1 s, characteristic for human circulation, was easily achievable in the microfluidic device, as shown by FIG. 6. When a solenoid valve was connected to the inlet syringe through a short and wide tubing segment, frame by frame analysis of the streakline images taken at a rate of 60 frames/s indicated that transitions between flow states corresponding to the driving pressures of $\Delta P_0$ and $\Delta P_0+P_1$ occurred within less than 30 ms. Abrupt changes of $\tau$ on time scales much shorter than the heartbeat period may not be physiological. To produce more gradual variations of shear stress, the solenoid valve was connected to a 10 cc inlet syringe by a long segment of thin tubing with a substantial resistance to air flow, R. The volume of the syringe above the liquid surface was used as a pneumatic capacitance, C, for the flow of air into and from the syringe, making a pneumatic equivalent of an electronic delay RC-circuit. The transition time, $t_{RC}$=RC, was adjusted by varying the length of the tubing segment and its resistance, R. As shown in FIG. 6, the time dependence of the shear stress in the pulsatile flow with $t_{RC}$ set at ~100 ms shows oscillations with more gradual changes in $\tau$ that more closely emulate the pulsing in blood circulation. The transition time could be extended further by increasing the value of R (not shown). For experiments with endothelial cells, when the perfusion medium must be saturated with air with 5% $CO_2$, the pressurized gas supplied to the inlet syringe is changed from air to a mixture of 5% $CO_2$ and 95% air.

EXAMPLE 2

Endothelial Cells Under Shear Flow

As a second test of the magnetic clamp and microfluidic chip, and to demonstrate their utility for live cell applications, a series of experiments were run with endothelial cells under shear flow, including experiments on the alignment of endothelial monolayer and healing of a scratch wound in it.

Figure 7:
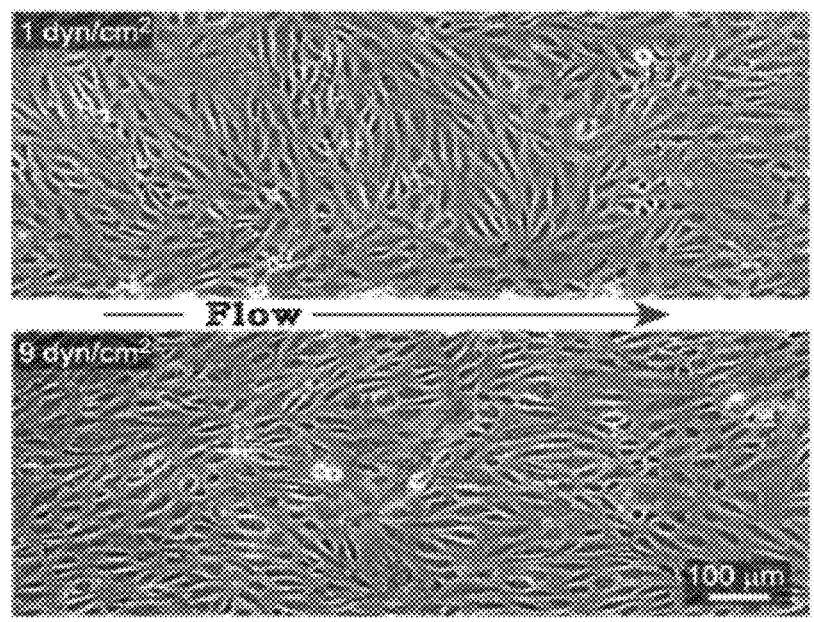
FIG. 7 is a set of micrographs of endothelial cells in two test regions of the microfluidic device after 15 hours of perfusion at shear stresses of 1 dyn/cm$^2$ (top) and 9 dyn/cm$^2$ (bottom).

The endothelium monolayer and the microchannel network were examined immediately after the clamp was closed and the device was sealed. Consistently, there was no visible damage to the endothelium at the bottom of the microchannels, no clogging of the relatively narrow resistance channels by cells, and no detached cells in the microchannels. Cells near side walls of the test regions did not suffer any detectable damage (or viability problems) from possible motion of the chip in the plane of the cover glass (twist) during the setup closing. Moreover, many cells immediately adjacent to the walls, whose parts were cut by the PDMS chip, rapidly recovered and became motile. To examine the viability and shear stress response of endothelial cells during prolonged perfusion experiments, the flow was driven by a constant hydrostatic pressure $\Delta P$=2.75 kPa and cells in all 8 test regions of the device, i.e., channels a, b, c and d divided into the narrower test region 54 and the wider test region 56, were exposed to shear stresses $\tau$=0.07-9 dyn/cm$^2$ (Table 1). Photographs were taken every 10 min using a 10× objective. Table 1 shows the shear stress at the substrate in internal areas of 8 test regions of the microfluidic device measured at $\Delta P$=2.75 kPa. Values of the relative shear stress are normalized to the shear stress in test region 1. The alignment along the flow direction was strong at the highest shear stress (9 dyn/cm$^2$) and became weaker at lower shear levels, with the cells oriented nearly randomly at $\tau$=1 dyn/cm$^2$ (FIG. 7). Both results were in agreement with the previous reports.

TABLE 1

| | Test region, # | | | | | | | |
|---|---|---|---|---|---|---|---|---|
| | 1<br>a-54 | 2<br>a-56 | 3<br>d-56 | 4<br>d-54 | 5<br>c-56 | 6<br>c-54 | 7<br>b-56 | 8<br>b-54 |
| Shear stress, dyn/cm$^2$ | 0.070 | 0.139 | 0.246 | 0.52 | 0.98 | 1.97 | 4.2 | 9.0 |
| Shear stress, relative | 1.0 | 1.99 | 3.51 | 7.4 | 14.0 | 28.1 | 60 | 127 |

A total of 6 experiments were performed under nearly identical conditions, with the flow applied for ~15 hr. Endothelial cells consistently showed good viability in all test regions, and the degree of their alignment along the flow was qualitatively reproduced at all of the shear stresses tested. Good cell viability in all test regions was also found in a single 40 hr perfusion experiment. Because the goal of these experiments was a proof of concept, no quantitative analysis of the dependence of the cellular alignment on $\tau$ was performed, and no attempt was made to achieve a maximal variation of the degree of alignment by adjusting the range of $\tau$. Upon completion of perfusion assays, after the clamp was disassembled and the PDMS chip was separated from the cover glass, endothelial cells on the substrate in the test regions remained intact. Consequently, the cells could be stained with various markers, fixed, and inspected again under a high resolution microscope. A potential problem of the present microfluidic chip, especially in low flow rate test regions, is that cells might be influenced by soluble factors released by endothelium in upstream regions, where the shear stress is different. This problem can be resolved by building a chip with a single test region per channel line connecting the inlet and outlet and by limiting the endothelium monolayer to the test region area.

Figure 8:
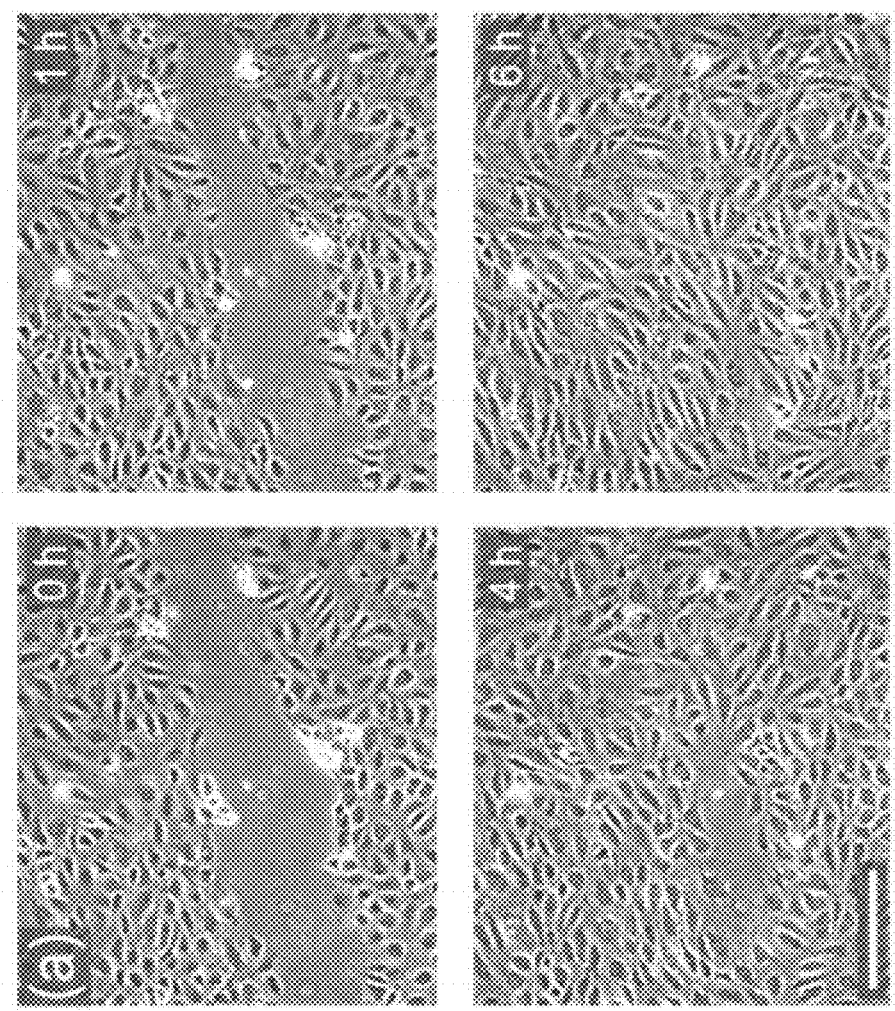
FIG. 8 is a series of phase-contrast micrographs showing the healing of a scratch wound in endothelium monolayer at different times. A flow with a substrate shear stress of 5 dyn/cm$^2$ was started at time 0, immediately after the device was sealed. The flow direction was vertically down.

The migration of endothelial cells plays an important role in vascular regeneration and remodeling. The endothelium monolayer wound healing assay tests the migration of endothelial cells towards a "wound", which is an area without cells, and the subsequent closure of the wound by a newly formed cell monolayer. Wounds were created by scratching endothelial monolayer using a 200 µl pipette tip (FIG. 8, top left). The wound healing was tested in the microfluidic device under a flow with τ=5 dyn/cm² directed perpendicularly to the scratch. The wound with a width varying between 100 and 200 µm was largely closed after 4 hr (FIG. 8, lower left) and completely healed after 6 hr of perfusion (FIG. 8, lower right). The healing time was in general agreement with previous reports. The analysis of migration trajectories of individual cells indicated that cells from the upstream edge of the wound migrated downstream at an average speed of 18 µm/hr compared with 11 µm/hr upstream migration speed of cells from the downstream edge of the wound, which was in agreement with previous reports.

EXAMPLE 3

Transfection of Cells

To demonstrate the feasibility of transfection of cells in the monolayer using a standard protocol and of the subsequent visualization of fluorescently tagged cells under shear flow, a plasmid encoding fluorescent protein pmAKAR3 was used. This protein has two separate fluorescent domains, cyan and yellow (CFP and YFP), and a phosphorylation target specific to protein kinase A (PKA). The distance between the two fluorescent domains is reduced when the target is phosphorylated. Therefore, this protein can serve as a Förster resonance energy transfer (FRET) reporter of intracellular PKA activity. Transient transfections of endothelium monolayer were performed using FuGENE 6 transfection reagent (Roche Diagnostics) and a protocol provided by the manufacturer. A mixture of the plasmid and FuGENE 6 reagent diluted with a serum-free medium (100 µL) was directly pipetted onto a cover glass with a confluent endothelial monolayer. The fraction of cells that were transfected and became fluorescent was 12-15% (typical values from three assays). No cells with a comparable level of fluorescence were observed with negative control transfection. Perfusion assays were performed 24 hours post-transfection.

Figure 9:
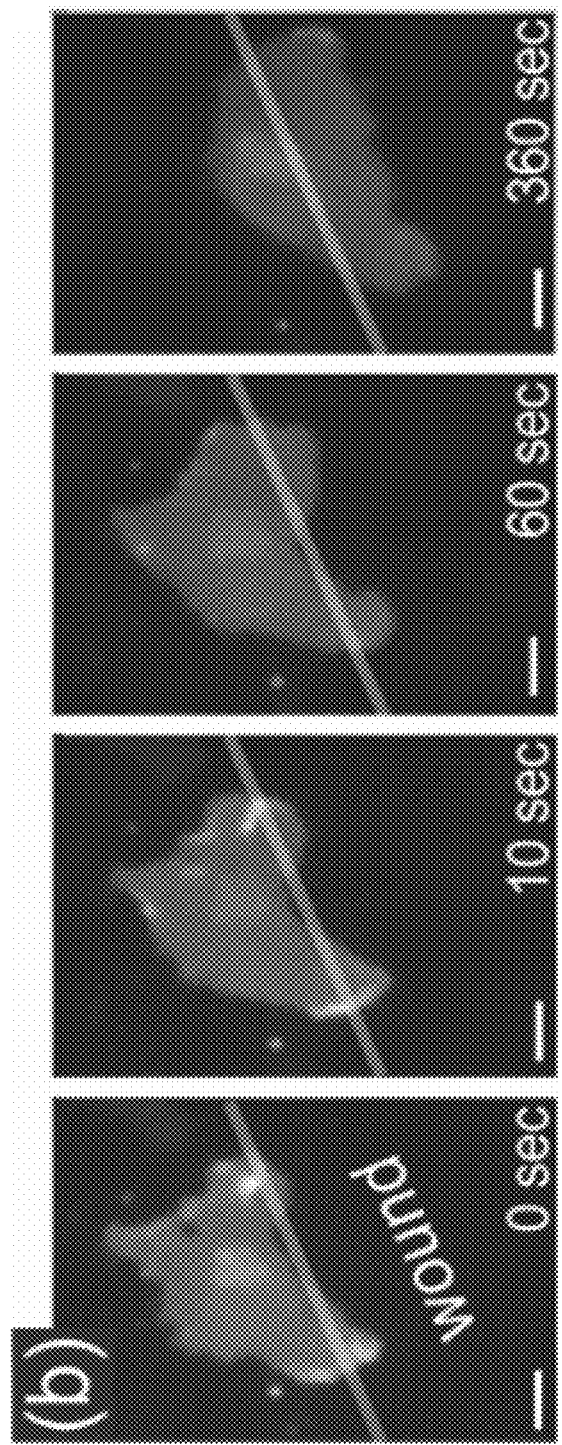
FIG. 9 is a series of real-time micrographs of an endothelial cell expressing fluorescent protein pmAKAR3 at the upstream edge of a scratch wound.

Immediately before the cover glass with the endothelium monolayer was sealed against the microfluidic chip in the magnetic clamp setup, a scratch wound was produced in the endothelium, as described above. After the microfluidic device was sealed, a perfusion flow through it was started. Transfected cells were imaged under the flow using fluorescence microscopy of CFP with a 20×/0.75 objective and the migration of fluorescent cells during the wound closing was be tracked in real time (FIG. 9). Whereas pmAKAR3 was only used as a fluorescent tag in these preliminary experiments, the strong fluorescent signal and high resolution of the cell images indicated that the proposed experimental procedure could be used to perform FRET microscopy of this protein. The FRET microscopy would make it possible to measure the levels of activity of PKA in individual cells (including those migrating towards a wound) with a sub-cellular resolution in real time under various shear stresses.

The inventive magnetic clamp assembly offers an alternative to the vacuum sealing technique introduced previously. A disadvantage of the magnetic clamp is that it requires a special setup, which needs to be machined and assembled. On the other hand, the proposed setup does not require a source of vacuum. Moreover, while somewhat bulky, the mechanical parts of the clamp make it possible to reduce to a minimum the hydrodynamic stresses generated during sealing of the device, thus making the setup compatible with weakly adherent cells. Another disadvantage of the proposed setup is the geometrical constraints it imposes on the microfluidic networks: the alignment of the inlets and outlets with the holes in the clamp cover and the fitting of the microchannel networks onto 25 mm cover glasses. However, for many practical cases, these constraints are relatively minor.

An additional aspect of the invention is a device and method for coating microfluidic chips with improved site density control. The same device and method provide means for coating a microfluidic chip with multiple different coatings on the same chip in well defined regions.

In an exemplary embodiment, a thin elastomer stencil or mask having one or more windows is removably bonded to the substrate. These windows, along with the region of the substrate framed by the windows, define "micro-cuvettes", which can be filled with small volumes (~10 µL) of solution to create a uniform coating. After incubation of the coating, the stencil is removed, leaving coated areas that are clearly defined and safely separated from each other.

Figure 10:
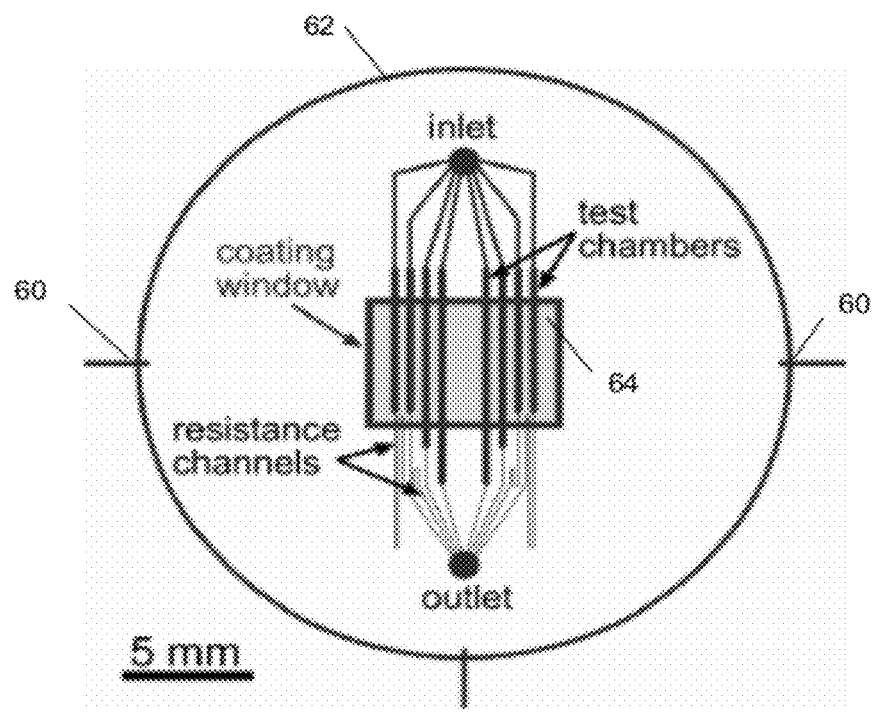
FIG. 10 is a diagram of a microfluidic device with a stencil used for substrate coating.

The stencils can be fabricated by creating a sheet by spin-coating a thin layer of PDMS pre-polymer, for example, 0.2 mm thick, onto a silicon wafer that has been photolithographically patterned to form a relief, e.g., 100 µm tall. The pattern on the wafer includes features for embossing grooves of a fixed depth into the surface of the sheet. The patterned wafer may also include an alignment mark for forming a corresponding mark in the sheet for aligning the stencil with respect to the glass substrate. In the example illustrated in FIG. 10, a 25 mm circle with three radial streaks 60 is used for alignment. In an exemplary implementation, at least one rectangle is formed in the middle of the sheet, defined by the relief pattern on the wafer. A single window 64 is illustrated in FIG. 10. After curing the PDMS and peeling the sheet off of the silicon wafer, a rectangular opening can be cut through the thickness of the sheet within the window by moving a scalpel or punch near, but inside, the perimeter of the rectangle. The resulting stencil may then be attached to a clean dry cover glass, with the window forming a 0.2 mm deep micro-cuvette in the middle of the cover glass. Because the area of the exposed glass surface is determined by the micro-fabricated grooves and not the actual cut, the exposed area will have a precisely-defined shape and area as along as the cut is within the boundaries defined by the grooves.

The substrate at the bottom of the micro-cuvette is coated by dispensing into the micro-cuvette a solution of molecules that form the coating. The solution can be dispensed with a micropipette or microsyringe. The amount of the solution required to fill the micro-cuvette is typically small, on the order of ~10 µL. After the solution is dispensed, the cuvette is covered from above (e.g., by a piece of microscope cover glass) to prevent evaporation. After an appropriate incubation time, the cover is removed, the micro-cuvette is purged and rinsed, and the stencil is separated from the substrate, leaving a well-defined coated area with sharp boundaries and uniform surface density of the deposited molecules. The final density of the molecules deposited on the substrate is highly reproducible and is controlled by their concentration in the solution and by the time of incubation.

The well defined size of the coated areas and the uniform surface density of the deposited molecules in the areas make it possible to accurately measure the surface density by using radio-labeled antibodies.

By using the stencils, multiple regions can be created with different coatings on one substrate, each with precisely defined area and sharp boundaries, by using multiple micro-cuvettes and by dispensing and incubating different solutions in different cuvettes. The coatings with sharp boundaries may be produced by using flaps on the stencils. Each flap can be individually detached from the substrate to expose a new region immediately adjacent to a previously coated area. To produce adjacent regions with different molecular coatings, the substrate in the region that is coated first can be blocked with some inert molecular coating (e.g., casein or albumin), before the second region is exposed.

The ability to create precisely controlled dimensions comes from the fact that the thickness of the elastomer stencils is greater than the depth of microfabricated grooves, with the boundaries of the cuvette being set by the lithographically defined grooves. Additionally, the micro-cuvettes may be used to coat the substrate rather than to plate cells.

EXAMPLE 4

Rolling of Monocytes on P-Selectin Coating

P-selectin coated substrates were created using micro-cuvettes 7.5 mm×5.5 mm by 0.2 mm deep, defined using the inventive stencils.

The glass surface was coated by dispensing 10 μL of a P-selectin solution into the micro-cuvette and incubating it for ~30 min. During the incubation, the micro-cuvette was covered by a small piece of thin glass to prevent evaporation of the solution and to suppress convective flow due to evaporative cooling. The micro-cuvette was subsequently rinsed with a phosphate buffer, and to prevent the adhesion of other macromolecules to the substrate, the substrate was blocked with a casein solution. Referring to FIG. 10, the coated cover glass was marked at the positions of the radial streaks 60, separated from the auxiliary chip, and immediately used as a substrate for a microfluidic chip (aligned against the streak marks), which was sealed against the cover glass in the magnetic clamp, with the P-selectin-coated area positioned at the bottom of test chambers of the microfluidic chip.

Figure 11:
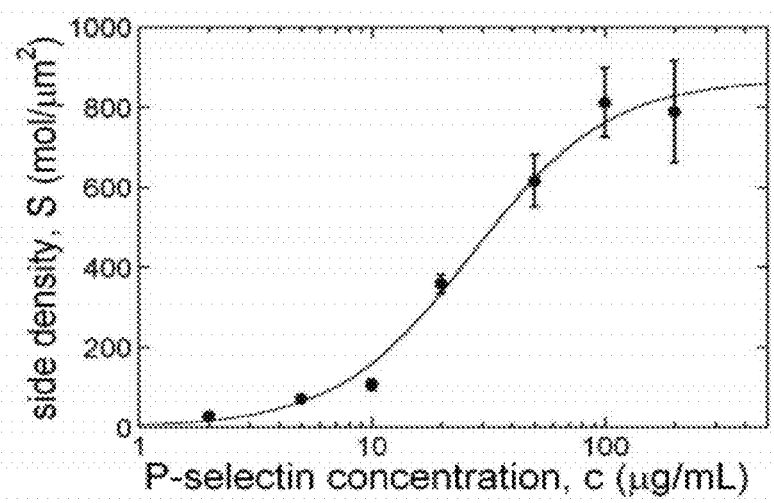
FIG. 11 is a plot of site density of a P-selectin coating created using the inventive stencil.

The P-selectin site density resulting from various solution concentrations was measured in a series of tests using radio-labeled anti-P-selectin antibodies (125I-labeled mAb RB40.34 at 5-10 μg/mL). The antibody solution was incubated in the micro-cuvette for 30 min after coating it with P-selectin (and rinsing with PBS and blocking with casein) and the micro-cuvette was then rinsed with PBS. The stencil was separated from the cover glass, and P-selectin with radio-labeled antibodies was washed from the glass surface by incubating the glass in 0.1 M NaOH/5% SDS in a 35 mm Petri dish. The solution from the Petri dish was then tested in the Gamma Counter, and the concentration of the radioactive antibodies was evaluated by comparing its radioactivity against solutions with known concentrations of the antibodies. The P-selectin site density was calculated based on the 7.5×5.5 mm surface area, assuming 1:1 ratio between P-selectin and antibody molecules. As can be seen in FIG. 11, the site density at a given P-selectin concentration was highly reproducible, and the site density as a function of the concentration followed a sigmoid curve reaching a saturated value of ~800 molecules/μm$^2$ at P-selectin concentrations >100 μg/mL.

The microfluidic device shown in FIG. 10 has two mirror-symmetric sets of channels connected to common inlet and outlet. There are four channels in each set with identical 30×300 μm test chambers and 30×50 μm wide resistance channels of different lengths downstream of the chambers, such that a differential pressure of 1 psi between the inlet and outlet results in substrate shear stresses, τ, of 2, 4, 6, and 8 dynes/cm2 in the test chambers. (Chambers closer to the outer sides have higher τ.) An assay in the device requires supply of blood at ~3 μL/min, and with an appropriate back pressure applied to the outlet, the device can be operated in an autoperfused mode. The device was used in experiments testing the rolling of leukocytes from whole mouse blood on P-selectin. The rolling was visualized with a 63×/1.4 objective and a digital CCD camera (up to 60 frames/s) under brightfield and fluorescence illumination (for GFP-expressing cells). The average rolling velocity was found to increase with τ, but the dependence of rolling on the site density was not studied in detail.

A modified version of the 0.2 mm thick PDMS stencil was fabricated to produce glass substrates with differently coated areas separated by a sharp boundary. This new stencil, illustrated in FIG. 12, which was used with the same microfluidic chip as before, has two adjacent rectangular windows 66, 68 in the middle. The first window 66 is cut before the stencil is attached to a cover glass. The stencil forms an 8×3 mm micro-cuvette on the cover glass, with boundaries precisely defined by the micro-fabricated grooves, as before. The glass surface at the bottom of the microcuvette is coated with adhesion molecules and rinsed as described above. After the coating is finished, the second window 68 is cut in the stencil without separating the stencil from the glass, and a second adhesion molecule solution is dispensed into the newly-formed L-shaped micro-cuvette. This technique can be used to coat the first area 66 with ICAM-1, to coat the entire L-shaped area (66 and 68 together) with P-selectin, and to subsequently block the entire glass substrate with casein, after the stencil is separated from the cover glass. Then, when blood is perfused through the microfluidic chip attached to the cover glass with the magnetic clamp, some monocytes in the left set of microfluidic test chambers will be rolling on P-selectin before encountering an area coated with both P-selectin and ICAM-1. In contrast, all monocytes in the right set of test chambers will encounter the substrate coated with both P-selectin and ICAM-1 without any prior interaction with P-selectin. Therefore, this test could reveal possible activation of α 4β1 integrin triggered by the interaction between P-selectin glycoprotein ligand-1 (PSGL-1) on monocytes and P-selectin on the substrate. The two rectangular areas 66, 68 can be coated completely independently of each other if the substrate in the first area 66 is blocked with a casein solution after it is coated. In a preliminary test of this method, the second area 68 was coated with FITC-conjugated casein, producing a sharp boundary of fluorescence between it and the first area 66, which was coated with plain casein. (As before, the boundary is defined by a microfabricated groove on the stencil.) Preliminary tests with radioactive antibodies indicated that the site densities of P-selectin and ICAM-1 in a given area are independently set by their respective concentrations in the solutions dispensed into the micro-cuvette and, therefore, are individually adjustable. Different types of stencils can be made to have substrates under two identical sets of channels coated at the same site density of one adhesion molecule (e.g. E-selectin), but different site densities of another molecule.

EXAMPLE 5

Rolling and Arrest of Neutrophils and Monocytes

Figure 12:
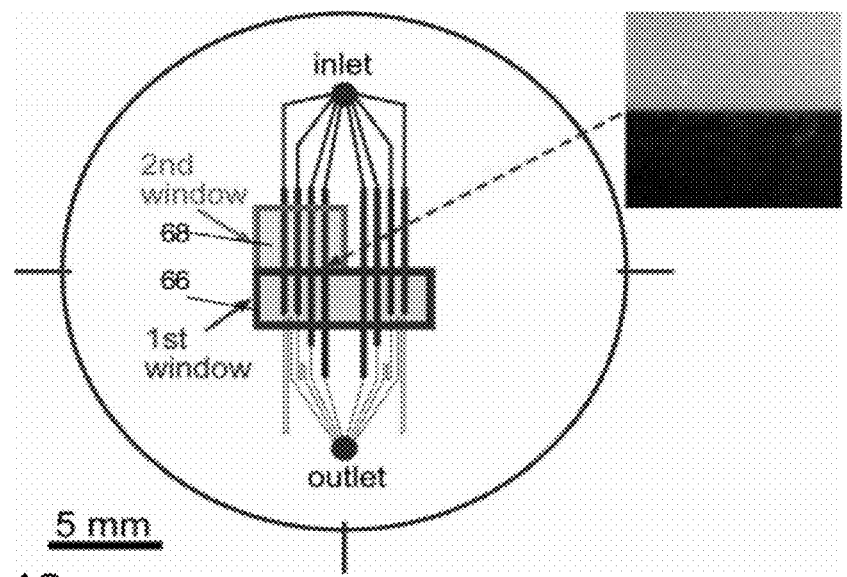
FIG. 12 is a diagram of a microfluidic device with a stencil that creates differently coated regions.

An example of application of the devices shown in FIGS. 10 and 12 are experiments on rolling and arrest of neutrophils and monocytes on substrates coated with adhesion molecules (P-selectin, ICAM-1, and VCAM-1) and chemokines (CXCL1, CCL5, and CX3CL1). A suspension of neutrophils is perfused over a substrate with a sharp boundary between an area blocked with casein and an area coated with a combination of P-selectin-ICAM-1-CXCL1, which is known to trigger neutrophil arrest. In the same device, the same neutrophil suspension is perfused over a region coated with P-selectin- ICAM, before it enters a P-selectin-ICAM-1-CXCL1-coated area (with a sharp boundary again). At a given shear stress (and flow rate), the characteristic distance from the CXCL1 boundary, at which first arrested cells are found, is expected to be proportional to the time required for activation of LFA-1 by CXCL1. Therefore, the phenotype of a genetic modification impairing the activation of LFA-1 could be an increase in this distance. The device in FIG. 12 tests the adhesion at four shear stresses in parallel, and this number can be further increased. Additional important experimental readouts can be the rate of neutrophil adhesion per unit area and their rolling distance before the arrest. The arrest of neutrophils on a substrate coated with P-selectin-ICAM-1-CXCL1 may be further modified by the presence of an upstream area coated with P-selectin-ICAM (e.g. by recruitment of neutrophils to the substrate). Therefore, a comparison of the arrests of wild-type and genetically modified neutrophils on such a two-area substrate could reveal further phenotypic changes introduced by the genetic modifications. The site densities of P-selectin-ICAM-1 can be varied in a controlled way between experiments to test the rolling and arrest at various conditions. Similar device can be used for experiments on monocyte arrest, with the substrates coated with mixtures of P-selectin-VCAM-1 (instead of P-selectin-ICAM-1) and with CCL5 and CX3CL1 used as the arrest chemokines.

Figures 13A, 13B:
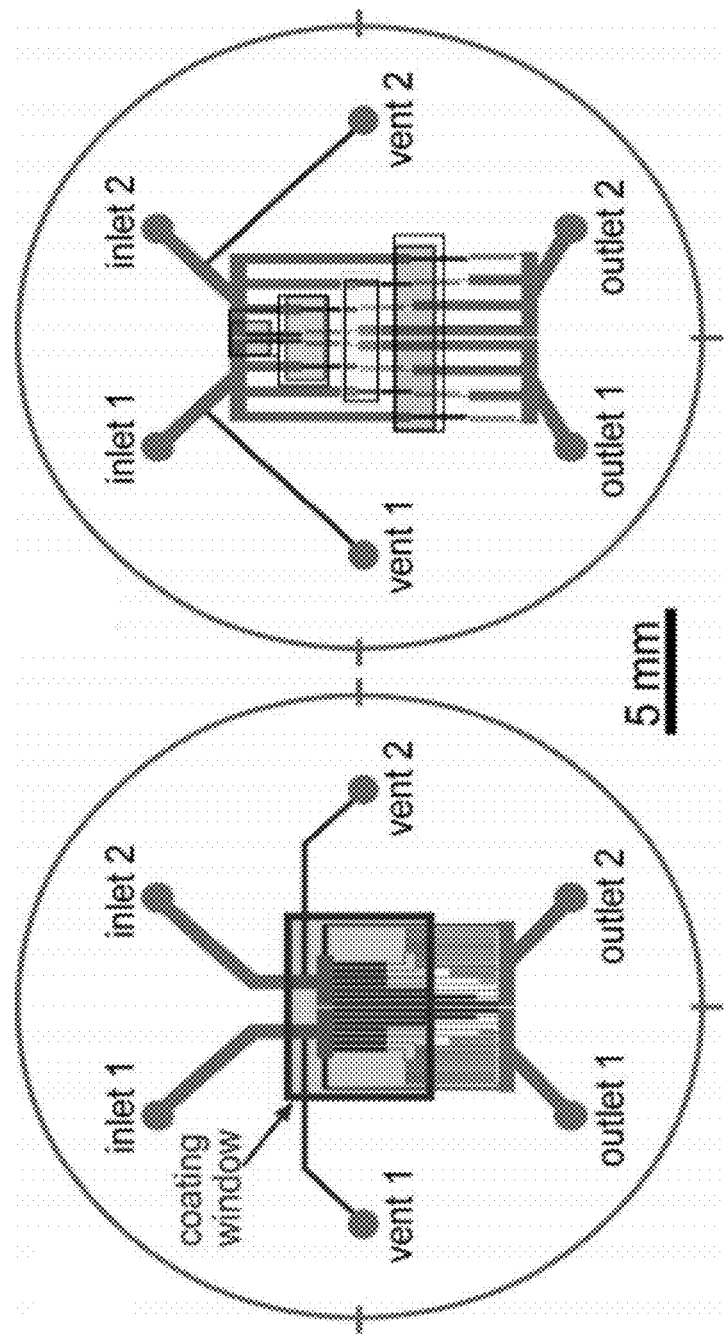
FIGS. 13a and 13b are diagrams of microfluidic devices with one and four coated regions, respectively.

FIGS. 13a and 13b show two examples of microfluidic devices for testing the adhesion of platelets to various substrates under shear. Both devices are sealed against substrates that are coated with adhesion molecules using micro-cuvettes formed by PDMS stencils reversibly bonded to the substrates. The first device (FIG. 13a) is adapted for the use with the magnetic clamp and with a cover glass coated using a PDMS stencil micro-cuvette. Two blood samples, e.g. from wild-type and genetically modified mice, are simultaneously fed to the inlets 1 and 2 and their dynamic adhesion to the substrate is tested in parallel in a 50-fold range of shear stress (e.g., from 1 to 50 dynes/cm2) in seven test chambers for each blood sample. Importantly, the coating with the micro-cuvette ensures identical site densities of the adhesion molecules in all test chambers. Moreover, as found in the studies for P-selectin coated substrates, the micro-cuvettes make the coatings highly reproducible and enable controlled variation of the site density of the adhesion molecules. The site densities of the adhesion molecules (collagen, fibrinogen, and VWF) can be measured using radio-labeled antibodies. The second prototype device (FIG. 13b) is built for parallel testing of two blood samples (fed to the inlets 1 and 2), but in contrast to the device in FIG. 13a has the same shear stress in all test chambers and only four test chambers for each blood sample. The shear stress could be $\tau \approx 3.5$ dynes/cm2, corresponding to the maximal difference in the adhesion between wild-type and activation-deficient $\alpha IIb\beta 3$. The device in FIG. 13b is used with a stencil having four separate micro-cuvettes, which enables testing of the adhesion of wild-type and genetically modified platelets to substrates with four different site densities of adhesion molecules in a single tests. Importantly, the set of four site densities will be exactly the same for both blood samples, because a given site density will be produced using the same micro-cuvette for test chambers from both sets (and thus for both blood samples).

Figure 14:
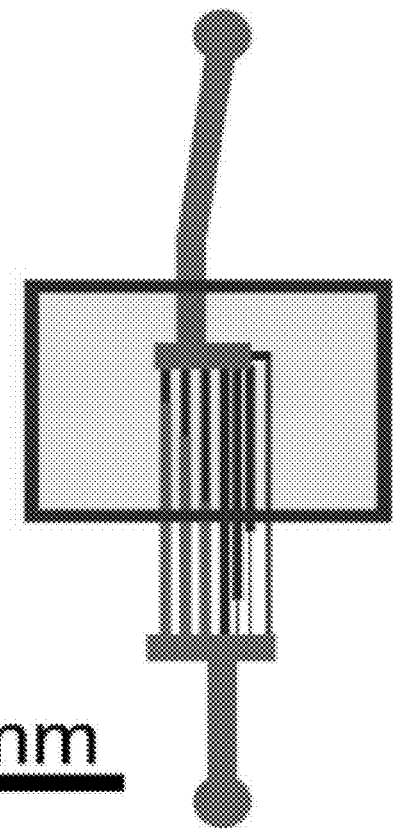
FIG. 14 is a diagram of a microfluidic device for studies of SVF-mediated platelet adhesion and aggregation.

Whereas the adhesion of platelets under shear to substrates coated with fibrinogen and collagen is most efficient at shear stresses of $\tau \sim 4\text{-}8$ dynes/cm$^2$, which are equivalent to shear rates of 100-200 s$^{-1}$ in whole blood, the adhesion of platelets to VWF and their aggregation mediated by the interaction of VWF and GPIb$\alpha$ has a threshold of a shear rate of ~10,000 s$^{-1}$ and $\tau \sim 400$ dynes/cm$^2$. Therefore, the microfluidic devices used in previous studies, in which the maximal value of $\tau$ is 50 dynes/cm$^2$ at a driving pressure 2.5 kPa, is modified for the experiments on VWF-mediated platelet adhesion and aggregation. Specifically, to avoid application of excessive driving pressures, the hydrodynamic resistances of the channel lines will be reduced by a factor of eight (FIG. 14). Therefore, a substrate shear stress of 1600 dynes/cm$^2$ (four times above the VWF-GPIb$\alpha$ interaction threshold) in test chambers with a cross-section of 24×200 µm will be achieved at a driving pressure of 10 kPa, which is four times below the pressure resistance limit of 40 kPa for microfluidic devices sealed with the magnetic clamp. At these conditions, the shear stress in 6 test chambers of the device in FIG. 14 ranges between 50 and 1600 dynes/cm$^2$, and the blood consumption is ~100 µL/min, with a sample of whole blood drawn from one mouse sufficient for a 3-5 min perfusion experiment. The blood consumption is reduced by half by applying a driving pressure of 5 kPa and reducing the maximal shear stress to 800 dynes/cm2 (still two times above the VWF-GPIb$\alpha$ interaction threshold).

EXAMPLE 6

Studies of Shear-Dependent Platelet Adhesion

Figure 15A:
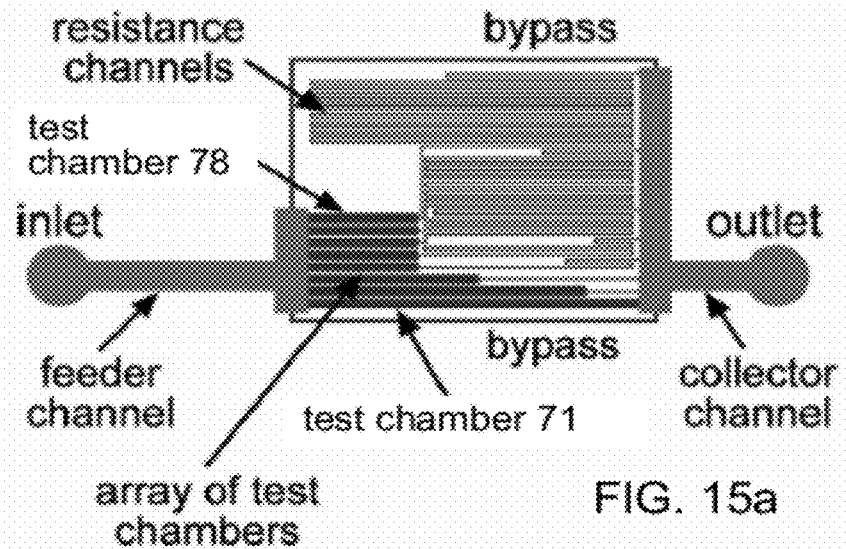
FIGS. 15a and 15b are diagrams of microfluidic devices used in a study of platelet adhesion.

The microfluidic device shown in FIG. 15a had one inlet, one outlet and an array of eight parallel test chambers. All test chambers, except for test chamber 71, were connected at their exits to resistance channels (24 µm deep and 40 µm wide). A test chamber and its resistance channel constituted a channel line. Each channel line was connected to the feeder channel on the upstream side and to the collector channel on the downstream side. The feeder and collector channels were both ~250 µm deep and ~500 µm wide, making their flow resistances negligible compared with those of the 24 µm deep channel lines, and providing equal pressures at the entrances and equal pressures at the exits of all eight channel lines. Thus the differential pressures, $\Delta P$, across the eight channel lines were all equal to each other and equal to the difference in pressure between the inlet and outlet of the device. The volumetric flow rate, Q, through a test chamber is found as $Q = \Delta P/R$ where R is the cumulative hydrodynamic resistance of the channel line. The values of R were designed to vary by a factor of 1.93 between adjacent channel lines, thus providing a 1.93-fold change in Q and shear stress, $\tau$, between adjacent test chambers, with a total 100-fold variation between the test chambers 71 and 78. Note that the microchannel architecture of device shown in FIG. 15a was essentially different from the architectures of the perfusion devices described previously, where shear stress variations were achieved by varying the width of the flow chambers, limiting the variations to about one order of magnitude.

Because of the large cross-section of the feeder channel as compared with the test chambers, the shear stress in the feeder channel was ~2 times lower than the lowest shear stress in the test chambers (found in the chamber 8), resulting in a minimal activation of platelets by shear stress prior to their arrival at the test chambers. Bypass channels at the edges of the test chamber array had relatively low flow resistance and were added to suppress the formation of air bubbles in the corners and to better synchronize the arrival of blood at different test chambers.

Figure 15B:
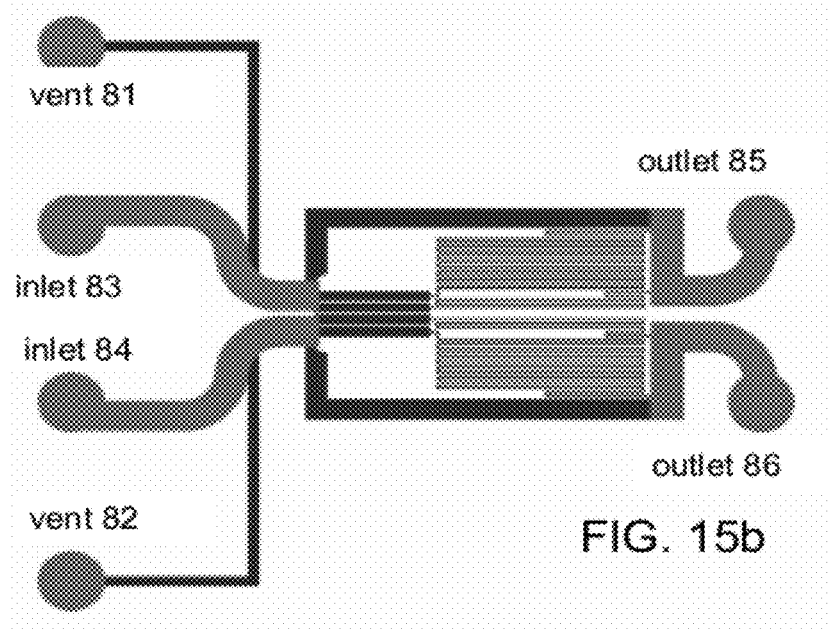

The microfluidic device of FIG. 15b had a set of two identical (mirror-symmetric) disconnected microchannel networks that were placed in close proximity of each other. Each network had an inlet, an outlet, and a vent port. Network A included inlet 83, outlet 85 and vent 81; network B consisted of inlet 84, outlet 86, and vent 82. Each network had two separate channel lines identical to two of the channel lines of the device of FIG. 15a.

Flow in the microfluidic devices was driven by differential hydrostatic pressure, ΔP, applied between the inlet and outlet, generated by gravity, and controlled within ~10 Pa. Care was taken to prevent platelet activation by avoiding exposure of blood to glass or metal components: blood and buffer solutions used in the experiments were kept in plastic syringes (1 mL and 10 mL) connected to the device through flexible TYGON® tubing (0.5 mm inner diameter) and short polyimide capillaries that were inserted into the device ports.

Function-blocking monoclonal antibody 1B5 against murine αIIbβ3 was from Dr. Barry Coller (Rockefeller University, New York, N.Y.). Monoclonal antibody AP-1 against human GP Ibα was from Dr. Thomas Kunicki (Scripps Research Institute, La Jolla, Calif.). Monoclonal antibody 5H1 against mouse P-selectin was from Dr. Rodger McEver (Oklahoma Medical Research Foundation, Oklahoma City, Okla.), and a polyclonal anti-mouse PSGL-1 blocking antibody was from Dr. Bruce Furie (Harvard University, Boston, Mass.). Integrilin, a selective antagonist to human or murine αIIbβ3 was from Dr. David Phillips (Portola Pharmaceuticals, Inc., South San Francisco, Calif.). Non-function-blocking antibodies to αIIb and granulocyte Ly-6 (Gr-1) were from Invitrogen/BD Biosciences (Carlsbad, Calif.), as were control IgG antibodies. Human plasma VWF was a gift from Dr. Zaverio Ruggeri (Scripps Research Institute, La Jolla Calif.). Fibrinogen was from Enzyme Research Co (South Bend, Ind.). All other reagents were from Sigma Chemical Co. (St. Louis, Mo.). 1.9 μm fluorescent beads, used to measure the flow rates by particle tracking, were purchased from Bangs Laboratories (Fishers, Ind.).

Human blood obtained from normal, drug-free donors was anticoagulated with 20 U/mL heparin, which maintains normal calcium concentrations and does not interfere with the platelet adhesion assays. Mouse blood was drawn by cardiac puncture into heparin-containing syringes. Mice deficient in integrin β3 (β3−/−) were obtained from Jackson Laboratories (Bar Harbor, Me.), and β3 knock-in mice (β3Y747A) were generated at University of California at San Diego. Wild-type mice (β3+/+) represented littermate controls. The platelet counts of mice of all three genotypes were similar.

Platelets were visualized by adding 2 μM mepacrine to whole blood to label dense granules. At high concentrations, mepacrine (which also labels leukocytes) may inhibit phospholipase A2. Nevertheless at 2 μM, platelet and leukocyte functions are maintained. For studies of platelet-granulocyte interactions, granulocytes in whole blood were additionally labeled with 16 μg/mL of a phycoerythrin (PE)-conjugated anti-Gr-1 antibody. No bleed-through occurred between the green fluorescence of mepacrine and red fluorescence of phycoerythrin. All inhibitors were added 25 min prior to onset of blood flow through the device, except ethanol control and prostaglandin E1 (PGE1), that were added 5 min prior to flow onset. To coat the glass substrata of the microfluidic devices with physiological matrices, the microchannels were filled with 20 μg/mL fibrinogen, 300 μg/mL acid-soluble Type I collagen or 10 μg/mL VWF, and incubated for 1 hour at room temperature. Subsequently, the devices were rinsed with an excessive amount of Hepes buffer (150 mM NaCl, 20 mM Hepes, pH 7.4) or rinsed with buffer and then blocked with 1% BSA for another 30 minutes, with similar results. The flow through the device was stopped by clamping the TYGON® tubing, and the outlet syringe was placed at a level of ~10 cm above the microscope stage. 200 μl of human or mouse blood with or without indicated inhibitors was gently drawn into a 1 cc plastic syringe through a TYGON® tubing line by pushing the plunger to ~⅕ of the syringe length, immersing the tubing into blood, pulling the plunger to the end of the syringe (thus creating a gauge pressure of −⅘ atm), waiting until the amount of blood in the syringe reached ~100 μL (plus ~100 μL in the tubing), and then quickly removing the plunger. The tubing was then connected to the device inlet. The inlet was pressurized at ΔP=2.5 kPa with respect to the outlet by raising the syringe with the blood so that the level of blood was 25 cm the above the level of the buffer in the outlet syringe. Alternatively, ~100 μL of mouse blood was loaded into a 0.5 mL Eppendorf tube that was sealed by a PDMS plug with two openings, for a luer stub connecting the tube to a source of compressed air with a pressure P=2.5 kPa, and for PE 10 polyethylene tubing. One end of the tubing line (that was ~10 cm long) was touching the bottom of the tube, and its other end was directly inserted into the device port. Because of small volume of blood in the polyethylene tubing line (~6 μL), almost entire blood sample loaded into the Eppendorf tube could be used for perfusion experiments.

For the device of FIG. 15a, flow of blood through the device was initiated by removing the clamp from the outlet tubing. Because of relatively low volume of buffer between the test channels and the tubing with the blood (~0.5 μL) and relatively high total volumetric flow rate through the device (~3.7 μL/min), the transient time of injection of blood into the test channels was only ~8 sec, which was substantially shorter than the duration of adhesion assays. In the device of FIG. 15b, there were four syringes with buffer connected to the outlets and vents of each of the two microchannel networks A and B through four separate TYGON® tubing lines. The lines connected to both outlets were initially clamped, and when the syringes with blood were connected to the inlets, the flow of blood was from the inlets to the vents. Once the buffer was purged from the channels connecting the inlets with the vents, and the channels were filled with whole blood, the vent tubing lines were clamped, completely stopping the flow through the device. The adhesion assay was started by simultaneous removal of the clamps from both outlet lines, thus starting flow of blood from inlets 83 and 84 to outlets 85 and 86, respectively. At that moment, blood in both networks was separated from the test chambers by small and equal volumes of buffer in the feeder channels. Therefore, the arrival of blood at the test chambers was synchronized within less than a second and occurred within less than a second from the moment of clamp removal. The duration of a perfusion experiment was <10 min, and the total consumption of blood during an experiment was <40 μL (<100 μL with occasional sample loss during tubing reconnection). Cells were counted as stably attached if they moved by less than one cell diameter in 10 seconds. To fix cells after an adhesion assay, the device was perfused with 3.7% formaldehyde and incubated for 10 minutes. The device was then disassembled and cover glasses were rinsed with Hepes buffer.

In the experiments with the device of FIG. 15a, the microfluidic device was mounted on a mechanical stage of a Nikon Diaphot inverted fluorescence microscope that was equipped with a Newport 850G linear actuator. The actuator was driving the stage in the direction perpendicular to the direction of flow in the test chambers and enabled moving the field of view of the microscope between different test chambers with a 5 μm positioning accuracy. Fluorescence microscopy was performed with a Nikon 100 W mercury light source and a GFP filter set (Ex470/Em525). The images of the platelets were acquired with a 63×, NA=1.4 oil immersion objective lens, a 0.42× video adapter, and a Sony SX900 IEEE1394 camera with a ½", 1280×960 pixel CCD array. An ND8 neutral density filter was used to reduce the intensity of fluorescence illumination and minimize platelet photoactivation.31 Motion of the stage and image acquisition were controlled through RS232 and IEEE1394 interfaces, respectively, using a code in LabView7.1 (National Instruments, Austin, Tex.). The stage was programmed to move in periodic scanning loops between the eight test chambers, with eight stops to take a fluorescence image of each chamber. One scanning loop took 16 sec that set the interval between consecutive images of individual test chambers. The images were acquired at ~400 μm from the beginning of the test chambers.

In the experiments with the device of FIG. 15b, when the adhesion of platelets from two different blood samples was simultaneously monitored, the device was mounted on a Nikon TE2000 inverted fluorescence microscope. The imaging was performed with a 40×, NA=1.3 PlanFluor oil immersion objective lens, a 0.42× Diagnostic Instruments video adapter, and a Hamamatsu C4742-95 IEEE1394 camera with a ⅔", 1280×1024 pixels CCD array. The field of view of this video microscopy setup was 500×375 μm that allowed imaging the entire width of two adjacent test chambers (440 μm including a 40 μm partition) with different blood samples in them. For fluorescence microscopy, a Nikon 100 W mercury light source was used with either a FITC filter set (Ex470/Em535) for stained platelets or a TRITC-HQ filter (Ex545/Em620) for stained granulocytes.

Quantification of adherent platelets, as well as velocity measurements by platelet tracking were performed using Image ProPlus (Media Cybernetics, Silver Spring, Md.) at the UCSD Neurosciences Core Microscopy Center (NINDS grant no. NS047101).

Flow velocity in the test chambers was measured using a 50% aqueous solution of ethylene glycol, with viscosity matching the standard viscosity of mouse blood, $\eta$=0.038 Ps, by seeding the solution with fluorescent beads and analyzing their streaklines. The measurements were done at the driving pressure, $\Delta P$=2.5 kPa, used in all platelet adhesion assays. The ratios between the values of maximal flow velocity, $v_{max}$, in adjacent test chambers in the device 1 were close to the target ratio of 1.93 (Table 1). Shear stresses in the test chambers, calculated as $\tau=4v_{max}\eta/h$, assuming a fully developed laminar shear flow, covered a range of 0.5-50 dyne/cm². The Reynolds number in the test chambers can be calculated as $Re=\rho vh/\eta$, where $\rho$=1.05 g/cm³ is the density of blood. The values of Re in the test chambers were always low, ~0.1 in the chamber 1 and <0.1 in the other chambers, suggesting that the flow was always laminar with negligible non-linear effects. The total volumetric flow rate through the device 1 was 3.7 μL/min.

In a steady laminar flow in a microchannel driven by differential pressure, shear stress is a function of the pressure, $\Delta P$, and channel geometry only and does not depend on the viscosity of the fluid. Therefore, the actual viscosity of the blood samples (that could be different from the standard value of 0.038 Ps) was not measured. For example, in a wide and shallow rectilinear channel, such as the test chamber 1 (FIG. 1A), in a region away from the side walls, the surface shear stress, $\tau$, is found from the equation $(\Delta P/L)h=2\tau$, where L is the channel length. The equation predicts a shear stress $\tau=\Delta Ph/(2L)$=50 dyne/cm² for the 6 mm long test chamber 1, the same as the value of $\tau$ measured experimentally. Because the surface shear stress is proportional to the channel depth, adhesion of platelets to the substrate is expected to reduce the shear stress. An adhered platelet has a height of ~1 μm, which is ~4% of the channel depth. All quantitative results reported in this paper were obtained when platelets covered only a part of the substrate surface and before they started aggregating (platelet monolayer), thus limiting the expected reduction of the surface shear stress due to the platelet adhesion to <4%.

Almost no platelets adhered to the glass substratum coated with BSA (≦5 platelets in a 180×240 μm field of view after 3 min perfusion at any of the shear stresses tested), indicating minimal non-specific adhesion. No platelets attached to PDMS walls of the test chambers. Platelet adhesion to physiological substrata may involve different braking, stabilization or thrombus growth events depending on the matrix presented. Therefore in order to assess the suitability of microfluidic devices for platelet adhesion studies, tests were run to determine whether the adhesion to three common physiologic matrices, VWF, fibrinogen, and collagen, occurred in a manner consistent with previous reports.

Figure 16A:
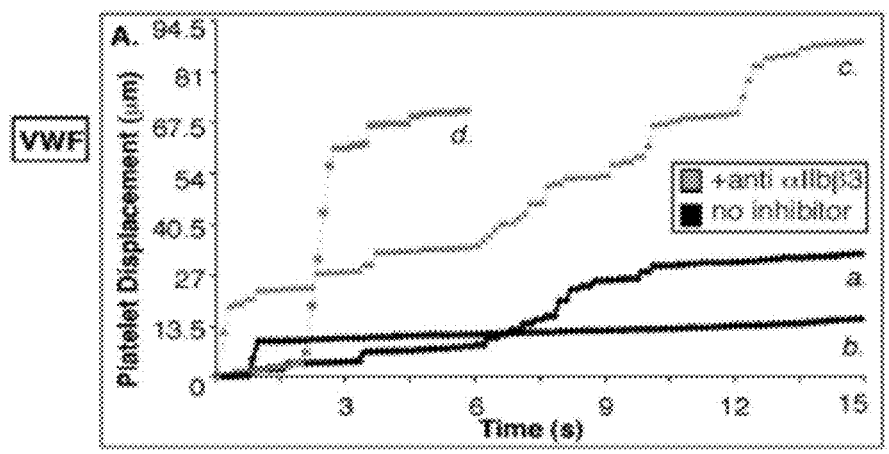
FIGS. 16a-16c are a plot of platelet displacement versus time (FIG. 16a), and histograms of the numbers of platelets attached at different shear stresses (FIGS. 16b and 16c).
Figure 16B:
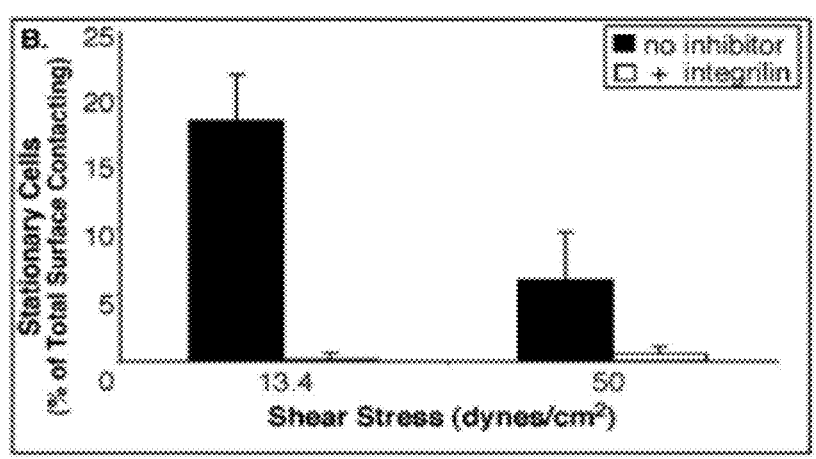

Platelets interacting with VWF-coated substrata first translocate on VWF via GPIb-IX-V tethering and subsequently induce signaling pathways that activate $\alpha IIb\beta 3$ for stable attachment. We used substrata coated with human VWF and assayed platelet adhesion to the substrata using human whole blood, because mouse platelets do not recognize human VWF and mouse VWF was not available. For an untreated blood sample, trajectories of individual platelets on VWF displayed intermittent intervals of translocation and rest, as shown in FIG. 16a. After 1 min of flow at 13.4 and 50 dynes/cm², respectively, 18.2±8 and 6.6±3% of platelets that interacted with the substratum within the field of view were stably attached to the substratum (FIG. 16b). Pretreatment of blood with an $\alpha IIb\beta 3$ antagonist, integrilin, abolished stable attachment, and platelets showed increased translocation and shortened rest periods. No platelet-VWF surface interactions occurred in the presence of an antibody against GPIbα (not shown), confirming that initial platelet interactions with VWF were dependent on GPIb-IX-V.

Figure 16C:
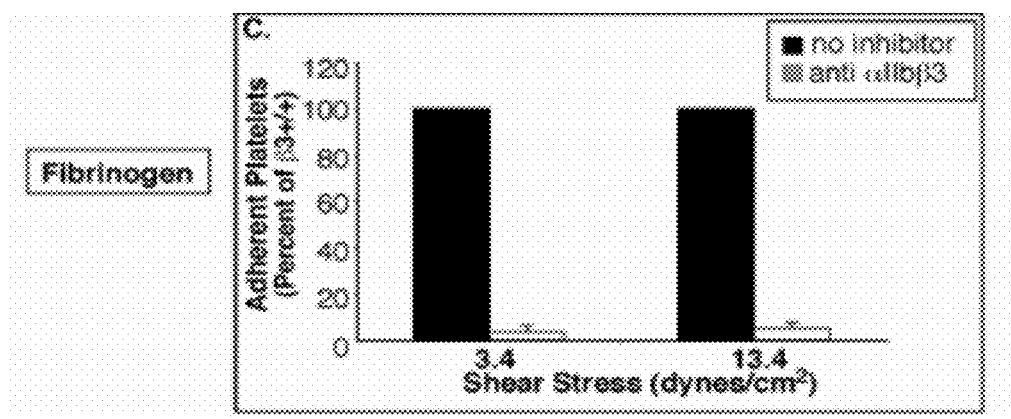

Because mouse models were to be used to investigate $\alpha IIb\beta 3$-dependent adhesion to fibrinogen and collagen, further validations were performed using mouse blood. The adhesion dynamics of mouse platelets to fibrinogen-coated substrata were assayed using human fibrinogen, which mouse platelets are known to recognize via $\alpha IIb\beta 3$; purified murine fibrinogen is not readily available. At both shear stresses tested, 3.4 and 13.4 dynes/cm², wild-type platelets were captured from the bulk of flowing blood and were immediately arrested on immobilized fibrinogen. As expected, this platelet adhesion to fibrinogen was $\alpha IIb\beta 3$ dependent, since it was almost completely inhibited (% I=89.0±2.4%) by a function-blocking antibody against $\alpha IIb\beta 3$ (FIG. 16c). Thus, the adhesion assay in the microfluidic device specifically reports on $\alpha IIb\beta 3$-dependent platelet arrest on a fibrinogen matrix.

Collagen stimulates platelets through the two primary collagen receptors, GP VI and integrin $\alpha 2\beta 1$, and induces $\alpha IIb\beta 3$ activation that is required for aggregation of platelets and their incorporation into thrombi. In agreement with the existing literature on platelet adhesion to collagen-coated substrata, wild-type platelets initially formed monolayers that induced platelet aggregation and thrombus formation.

The results of the assays described above agree with previous reports on platelet interactions with VWF, fibrinogen, and collagen-coated substrata, and thus indicate that the proposed microfluidic devices are appropriate tools to study shear-dependent platelet adhesion.

EXAMPLE 7

Quantification of Platelet-Granulocyte Interactions

To test whether the microfluidic devices could be used to study heterocellular interactions, dynamic attachment of PE-anti-Gr1-labeled granulocytes to platelets adherent to collagen was examined. Importantly, in the assay, platelet-granulocyte interactions evolved naturally over time from cellular levels present in blood and no exogenous agonists were added to activate cells. Granulocytes were often entrapped in growing platelet thrombi in $\beta3^{+/+}$ blood (FIG. 5A), making it difficult to quantify granulocyte interactions with platelets. No thrombi formed from $\beta3^{-/-}$ blood, however. Therefore, rolling velocities and the subsequent attachment of granulocytes on $\beta3^{-/-}$ collagen-adherent platelet monolayers could both be determined. Transient platelet-granulocyte interactions were observed even at $\tau>30$ dynes/cm$^2$ and were often accompanied by extension and retraction of granulocyte tethers.

Mean rolling velocities of granulocytes on collagen-adherent $\beta3^{-/-}$ platelets increased with shear stress, from $3.0\pm0.7$ μm/s at 3.4 dynes/cm2 to $7.2\pm1.2$ μm/s at 13.4 dynes/cm$^2$ (n=5, p<0.01). At 3.4 dynes/cm$^2$, initial interactions led to stable attachment of a substantial portion of granulocytes ($27.1\pm7.2\%$), but at 3.4 dynes/cm$^2$ the attachment was minimal. Interactions of granulocytes with β3−/− platelets were abolished by antibodies against P-selectin and PSGL-1, but not by control antibodies (% rolling granulocytes relative to IgG control at 3.4 and 13.4 dynes/cm$^2$, respectively: $1.3\pm0.8\%$, and 0% for anti P-selectin; $7.9\pm3.4\%$ and $3.4\pm3.0\%$ for anti-PSGL-1; n=3, p<0.01). Therefore, the granulocyte-platelet interactions were dependent on P-selectin and PSGL-1, in agreement with previous reports.38, 39 On the other hand, treatment of $\beta3^{+/+}$ platelets with anti-P-selectin and anti-PSGL-1 antibodies did not entirely prevent the presence of granulocytes in thrombi derived from $\beta3^{+/+}$ blood, providing further evidence for non-specific $\beta3^{+/+}$ granulocyte entrapment in the thrombi. No rolling of granulocytes was observed on platelets attached to fibrinogen for either $\beta3^{+/+}$ or $\beta3^{-/-}$ blood, presumably due to lower surface expression of P-selectin compared to platelets adherent to collagen.

The microfluidic devices according to the present invention are made of single casts of PDMS sealed with a cover glass and they can be made at low cost in amounts sufficient for an extended series of laboratory experiments. The devices are also easily recycled by detaching the PDMS chip from the cover glass, cleaning the chip in a mild detergent, and sealing it with a new cover glass. The flow in the devices is driven by hydrostatic pressure, making them simple to operate, particular one that has a single inlet and outlet. When a polyethylene (PE) tubing of an appropriate diameter is inserted into the device inlet, the tubing is held in place and makes an instantaneous sealed connection. The insertion of the other end of the tubing line into an artery of an anesthetized mouse would convert the device into an ex-vivo autoperfusion flow chamber, reducing to a minimum the variation of blood between the circulation and the microfluidic test chambers. In addition to the dynamic adhesion of platelets, the inventive devices could also be used to study rolling and substrate adhesion of other cell types, e.g., neutrophils, without the need of sacrificing donor mice. Another possible application of the devices is studies of formation of platelet aggregates (thrombi) on various substrates at controlled flow conditions. Reduction of the test chamber cross-sections would further reduce the sample volumes and potentially enable adhesion assays in shear flow with blood from genetically amenable organisms, such as zebra fish. A possible clinical application of the proposed devices is for testing blood of neonates and young patients, where blood availability is limited.

References—Incorporated Herein by Reference
1. B. G. Chung, L. A. Flanagan, S. W. Rhee, P. H. Schwartz, A. P. Lee, E. S. Monuki and N. L. Jeon, *Lab On A Chip*, 2005, 5, 401-406.
2. P. J. Hung, P. J. Lee, P. Sabounchi, R. Lin and L. P. Lee, *Biotechnology And Bioengineering*, 2005, 89, 1-8.
3. A. Groisman, C. Lobo, H. Cho, J. K. Campbell, Y. S. Dufour, A. M. Stevens and A. Levchenko, *Nature Meth.*, 2005, 2, 685-689.
4. P. C. H. Li, L. de Camprieu, J. Cai and M. Sangar, *Lab On A Chip*, 2004, 4, 174-180.
5. A. Tourovskaia, X. Figueroa-Masot and A. Folch, *Lab On A Chip*, 2005, 5, 14-19.
6. S. Usami, H. H. Chen, Y. H. Zhao, S. Chien and R. Skalak, *Annals of Biomedical Engineering*, 1993, 21, 77-83.
7. S. K. Murthy, A. Sin, R. G. Tompkins and M. Toner, *Langmuir*, 2004, 20, 11649-11655.
8. H. Lu, L. Y. Koo, W. M. Wang, D. A. Lauffenburger, L. G. Griffith and K. F. Jensen, *Anal Chem*, 2004, 76, 5257-5264.
9. E. Gutierrez and A. Groisman, *Analytical Chemistry*, 2007, 79, 2249-2258.
10. M. A. Corson, N. L. James, S. E. Latta, R. M. Nerem, B. C. Berk and D. G. Harrison, *Circulation Research*, 1996, 79, 984-991.
11. S. R. P. Gudi, C. B. Clark and J. A. Frangos, *Circulation Research*, 1996, 79, 834-839.
12. A. J. Kanai, H. C. Strauss, G. A. Truskey, A. L. Crews, S. Grunfeld and T. Malinski, *Circulation Research*, 1995, 77, 284-293.
13. R. Alon, P. D. Kassner, M. W. Carr, E. B. Finger, M. E. Hemler and T. A. Springer, *Journal of Cell Biology*, 1995, 128, 1243-1253.
14. P. Carmeliet, *Nat Med*, 2000, 6, 389-395.
15. V. A. Korshunov, S. M. Schwartz and B. C. Berk, *Arterioscler Thromb Vasc Biol*, 2007, 27, 1722-1728.
16. K. S. Cunningham and A. I. Gotlieb, *Lab Invest*, 2005, 85, 9-23.
17. K. R. Stenmark and R. P. Mecham, *Annu Rev Physiol*, 1997, 59, 89-144.
18. S, Noria, D. B. Cowan, A. I. Gotlieb and B. L. Langille, *Circ Res*, 1999, 85, 504-514.
19. E. Tzima, M. Irani-Tehrani, W. B. Kiosses, E. Dejana, D. A. Schultz, B. Engelhardt, G. Cao, H. DeLisser and M. A. Schwartz, *Nature*, 2005, 437, 426-431.
20. J. Y. Shyy and S. Chien, *Circ Res*, 2002, 91, 769-775.
21. E. Tzima, M. A. del Pozo, S. J. Shattil, S. Chien and M. A. Schwartz, *Embo J*, 2001, 20, 4639-4647.
22. J. N. Lee, X. Jiang, D. Ryan and G. M. Whitesides, *Langmuir*, 2004, 20, 11684-11691.
23. S. W. Rhee, A. M. Taylor, C. H. Tu, D. H. Cribbs, C. W. Cotman and N. L. Jeon, *Lab on a Chip*, 2005, 5, 102-107.
24. B. D. Plouffe, D. N. Njoka, J. Harris, J. H. Liao, N. K. Horick, M. Radisic and S. K. Murthy, *Langmuir*, 2007, 23, 5050-5055.
25. U. Y. Schaff, M. M. Q. Xing, K. K. Lin, N. Pan, N. L. Jeon and S. I. Simon, *Lab on a Chip*, 2007, 7, 448-456.
26. J. W. Song, W. Gu, N. Futai, K. A. Warner, J. E. Nor and S. Takayama, *Analytical Chemistry*, 2005, 77, 3993-3999.
27. J. K. Tsou, R. M. Gower, H. J. Ting, U. Y. Schaff, M. F. Insana, A. G. Passerini and S. I. Simon, *Microcirculation*, 2008, 15, 311-323.
28. D. M. Spence, N. J. Torrence, M. L. Kovarik and R. S. Martin, *Analyst*, 2004, 129, 995-1000.
29. C. J. Ku, T. D. Oblak and D. M. Spence, *Analytical Chemistry*, 2008, 80, 7543-7548.
30. V. Saarela, S. Franssila, S. Tuomikoski, S. Marttila, P. Ostman, T. Sikanen, T. Kotiaho and R. Kostiainen, *Sensors and Actuators B-Chemical*, 2006, 114, 552-557.

31. E. M. Lucchetta, J. H. Lee, L. A. Fu, N. H. Patel and R. F. Ismagilov, *Nature,* 2005, 434, 1134-1138.
32. H. Bang, W. G. Lee, J. Park, H. Yun, J. Lee, S. Chung, K. Cho, C. Chung, D. C. Han and J. K. Chang, *Journal of Micromechanics and Microengineering,* 2006, 16, 708-714.
33. A. Khademhosseini, J. Yeh, G. Eng, J. Karp, H. Kaji, J. Borenstein, O. C. Farokhzad and R. Langer, *Lab on a Chip,* 2005, 5, 1380-1386.
34. M. Le Berre, C. Crozatier, G. V. Casquillas and Y. Chen, *Microelectronic Engineering,* 2006, 83, 1284-1287.
35. C. Crozatier, I. Tapsoba, L. P. Xu, D. Han, L. Sensebe and Y. Chen, *Microelectronic Engineering,* 2007, 84, 1694-1697.
36. M. I. Latz, M. Bovard, V. VanDelinder, E. Segre, J. Rohr and A. Groisman, *Journal Of Experimental Biology,* 2008, 211, 2865-2875.
37. C. J. Wang, X. Li, B. Lin, S. Shim, G. L. Ming and A. Levchenko, *Lab On A Chip,* 2008, 8, 227-237.
38. A. W. Orr, B. P. Helmke, B. R. Blackman and M. A. Schwartz, *Developmental Cell,* 2006, 10, 11-20.
39. A. W. Orr, B. P. Helmke, B. R. Blackman and M. A. Schwartz, *Dev Cell,* 2006, 10, 11-20.
40. S. Chien, *Mol Cell Biomech,* 2008, 5, 1-8.
41. P. Carmeliet, *Nature Medicine,* 2003, 9, 653-660.
42. D. E. Morales, K. A. McGowan, D. S. Grant, S. Maheshwari, D. Bhartiya, M. C. Cid, H. K. Kleinman and H. W. Schnaper, *Circulation,* 1995, 91, 755-763.
43. E. Tkachenko, A. Elfenbein, D. Tirziu and M. Simons, *Circ Res,* 2006, 98, 1398-1404.
44. S. Li, N. F. Huang and S. Hsu, *Journal Of Cellular Biochemistry,* 2005, 96, 1110-1126.
45. M. D. Allen and J. Zhang, *Biochem Biophys Res Commun,* 2006, 348, 716-721.
46. B. R. Blackman, K. A. Barbee and L. E. Thibault, *Annals of Biomedical Engineering,* 2000, 28, 363-372.
47. B. R. Blackman, G. Garcia-Cardena and M. A. Gimbrone, *Journal of Biomechanical Engineering-Transactions of the Asme,* 2002, 124, 397-407.
48. G. H. Dai, M. R. Kaazempur-Mofrad, S, Natarajan, Y. Z. Zhang, S. Vaughn, B. R. Blackman, R. D. Kamm, G. Garcia-Cardena and M. A. Gimbrone, *Proceedings of the National Academy of Sciences of the United States of America,* 2004, 101, 14871-14876.
49. T. C. Merkel, V. I. Bondar, K. Nagai, B. D. Freeman and I. Pinnau, *Journal Of Polymer Science Part B-Polymer Physics,* 2000, 38, 415-434.

The invention claimed is:

1. In a microfluidic system, a device for sealing a microfluidic chip having a face with at least one test region comprising a plurality of microchannels, the device comprising:
a magnetic clamp for exerting a reproducible and uniform pressure on the microfluidic chip to releasably seal the chip with minimal mechanical perturbation to cells on the substrate, wherein the magnetic clamp comprises:
a base having an open center, the base comprising a magnetically-attractable material;
a window supported within the open center, the window adapted for viewing the face of the microfluidic chip through the window;
a ring disposed over the base, the ring having a center opening corresponding to the open center of the base;
a plurality of magnets distributed around the ring for generating a magnetic force drawing the ring against the base;
a transparent disk disposed on top of the ring, the disk having an inlet and an outlet adapted for connection to a fluid medium reservoir for introducing and removing the fluid medium, wherein the disk, the window, the center opening of the ring and the open center of the base define a cavity for enclosing the microfluidic chip with the face of the microfluidic chip with the at least one test region abutting the window; and
an elastomer cushion disposed within the cavity between the disk and a backside of the microfluidic chip;
wherein the magnetic force compresses the elastomer cushion against the microfluidic chip so that the at least one test region is sealed against the window.

2. The device of claim 1, further comprising a plurality of adjustable spacers for creating a gap between the base and the ring for countering compression of the elastomer cushion to adjust pressure against the microfluidic chip.

3. The device of claim 2, wherein the plurality of adjustable spacers comprises screws threadably retained within the ring so that an end of the screws presses against the ring to apply a separating force between the ring and the base, and rotation of the screw adjusts the separating force to adjust the gap.

4. The device of claim 1, further comprising a plurality of alignment features for aligning the base and the ring.

5. The device of claim 4, wherein the alignment features comprise pins extending from the base to mate with corresponding openings in the ring.

6. The device of claim 1, further comprising a channel in fluid communication with each of the inlet and the outlet, each channel having a first end and a second end, wherein the second end terminates near an inner surface of the window so that the fluid medium is communicated to the microfluidic chip.

7. The device of claim 6, wherein the first end of the channel defines a bubble chamber, and wherein the bubble chamber is releasably sealed.

8. The device of claim 1, wherein the window comprises a microscope cover glass.

9. The device of claim 1, wherein the elastomer cushion is formed from silicone having a uniform thickness to within about 0.1 mm.

10. The device of claim 9, wherein the silicone is transparent.

11. The device of claim 1, wherein the elastomer cushion is attached to the disk using an adhesive.

12. The device of claim 1, wherein the ring is formed from brass.

13. The device of claim 1, wherein the base is formed from a magnetic stainless steel.

14. A microfluidic system comprising:
an elastomeric chip having a plurality of microchannels molded therein;
a clamp having a cavity for retaining the elastomeric chip for observation of fluids within the microchannels, the clamp comprising:
a base having an open center for supporting a window adapted for observing the fluids, the base comprising a magnetically-attractable material;
a ring having a center opening aligned with the open center of the base;
magnets distributed around the ring for generating a force drawing the base toward the ring;
a transparent disk disposed on top of the ring, the disk having an inlet and an outlet adapted for connection to a fluid medium reservoir for introducing and removing the fluid medium, wherein the disk, the window, the center opening of the ring and the open center of the base define the cavity; and an elastomer cushion disposed within the cavity between the disk and a backside of the microfluidic chip;

wherein the force generated by the magnets compresses the elastomer cushion against the elastomeric chip so that the microchannels are pressed against the window.

15. The microfluidic system of claim 14, further comprising a plurality of adjustable spacers for creating a gap between the base and the ring for countering compression of the elastomer cushion to adjust pressure against the elastomeric chip.

16. The microfluidic system of claim 15, wherein the plurality of adjustable spacers comprises screws threadably retained within the ring so that an end of the screws presses against the ring to produce a separating force between the ring and the base, and wherein rotation of the screw adjusts the separating force to adjust the gap.

17. The microfluidic system of claim 14, further comprising a plurality of alignment features for aligning the base and the ring.

18. The microfluidic system of claim 17, wherein the alignment features comprise pins extending from the base to mate with corresponding openings in the ring.

19. The microfluidic system of claim 14, further comprising a channel in fluid communication with each of the inlet and the outlet, each channel having a first end and a second end, wherein the second end terminates near an inner surface of the window so that the fluid medium is communicated to the microchannels of the elastomeric chip.

20. The microfluidic system of claim 19, wherein the first end of the channel defines a bubble chamber, and wherein the bubble chamber is releasably sealed.

21. The microfluidic system of claim 14, wherein the window comprises a microscope cover glass.

22. The microfluidic system of claim 14, wherein the elastomer cushion is formed from transparent silicone having a uniform thickness to within about 0.1 mm.

23. The microfluidic system of claim 14, wherein the elastomer cushion is attached to the disk using an adhesive.

24. The microfluidic system of claim 14, wherein the ring is formed from brass.

25. The microfluidic system of claim 14, wherein the base is formed from a magnetic stainless steel.

26. The microfluidic system of claim 14, wherein the elastomeric chip is formed from PDMS.

27. The microfluidic system of claim 14, wherein the elastomeric chip has one or more micro-cuvettes defined thereon by releasably applying a flexible stencil to the face of the chip, the stencil having at least one window through which a coating of an adhesion molecule solution is applied, wherein, after removal of the stencil, the coating applied within at least one window comprises a micro-cuvette.

28. The microfluidic system of claim 27, wherein the flexible stencil has a plurality of windows formed therein, and a different adhesion molecule solution is applied to each window.

* * * * *